US011885803B2

(12) United States Patent
Kamei et al.

(10) Patent No.: US 11,885,803 B2
(45) Date of Patent: *Jan. 30, 2024

(54) METHODS AND DEVICES FOR ANALYTE COLLECTION, EXTRACTION, CONCENTRATION, AND DETECTION FOR CLINICAL APPLICATIONS

(71) Applicant: The Regents of the University of California, Oakland, CA (US)

(72) Inventors: Daniel Takashi Kamei, Monterey Park, CA (US); Yin To Chiu, Irvine, CA (US); Benjamin Ming Wu, San Marino, CA (US); Garrett L. Mosley, Newport Beach, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/673,530

(22) Filed: Feb. 16, 2022

(65) Prior Publication Data

US 2022/0252598 A1    Aug. 11, 2022

Related U.S. Application Data

(62) Division of application No. 15/756,542, filed as application No. PCT/US2016/050257 on Sep. 2, 2016, now Pat. No. 11,287,426.

(60) Provisional application No. 62/214,801, filed on Sep. 4, 2015.

(51) Int. Cl.
| | |
|---|---|
| *G01N 33/569* | (2006.01) |
| *G01N 33/543* | (2006.01) |
| *G01N 33/483* | (2006.01) |
| *G01N 33/49* | (2006.01) |
| *G01N 33/493* | (2006.01) |

(52) U.S. Cl.
CPC ... *G01N 33/56927* (2013.01); *G01N 33/4833* (2013.01); *G01N 33/49* (2013.01); *G01N 33/493* (2013.01); *G01N 33/54388* (2021.08); *G01N 33/54391* (2021.08); *G01N 33/569* (2013.01); *G01N 33/56944* (2013.01); *G01N 33/56961* (2013.01); *G01N 33/56983* (2013.01)

(58) Field of Classification Search
None
See application file for complete search history.

(56) References Cited

U.S. PATENT DOCUMENTS

| | | |
|---|---|---|
| 5,141,850 A | 8/1992 | Cole et al. |
| 6,194,221 B1 | 2/2001 | Rehg et al. |
| 6,436,722 B1 | 8/2002 | Clark et al. |
| 6,855,561 B2 | 2/2005 | Jerome et al. |
| 6,924,153 B1 | 8/2005 | Boehringer et al. |
| 6,979,576 B1 | 12/2005 | Cheng et al. |
| 7,179,657 B2 | 2/2007 | Jerome et al. |
| 7,226,793 B2 | 6/2007 | Jerome et al. |
| 7,459,314 B2 | 12/2008 | Guo et al. |
| 7,537,937 B2 | 5/2009 | Jerome et al. |
| 7,553,675 B2 | 6/2009 | Jerome et al. |
| 7,666,614 B2 | 2/2010 | Cheng et al. |
| 7,794,656 B2 | 9/2010 | Liang et al. |
| 7,867,780 B2 | 1/2011 | Jones et al. |
| 7,932,099 B2 | 4/2011 | Egan et al. |
| 8,003,765 B2 | 8/2011 | Pentyala |
| 8,030,091 B2 | 10/2011 | Jerome et al. |
| 8,193,002 B2 | 6/2012 | Guo et al. |
| 8,377,710 B2 | 2/2013 | Whitesides et al. |
| 8,445,293 B2 | 5/2013 | Babu et al. |
| 8,603,832 B2 | 12/2013 | Whitesides et al. |
| 8,628,729 B2 | 1/2014 | Carrilho et al. |
| 8,828,739 B2 | 9/2014 | Guo et al. |
| 9,193,988 B2 | 11/2015 | Whitesides et al. |

(Continued)

FOREIGN PATENT DOCUMENTS

| | | |
|---|---|---|
| CN | 102224160 A | 10/2011 |
| CN | 102584933 A | 7/2012 |

(Continued)

OTHER PUBLICATIONS

Ahmed (2015) "Hydrogel: Preparation, characterization, and applications: A review" J. Adv. Res., 6:105-121.
Arrer et al. (2002) "β-Trace Protein as a Marker for Cerebrospinal Fluid Rhinorrhea" Clin. Chem. 48(6):939-941.
AU Examination report No. 1 dated May 24, 2021 issued in AU 2020201579.
AU Examination report No. 1 dated Oct. 8, 2019 issued in AU 2015226930.
AU Office Action dated Nov. 4, 2021 issued in AU 2016318103.
Bachmann et al. (2002) "Predictive values of beta-trace protein (prostaglandin D synthase) by use of laser-nephelometry assay for the identification of cerebrospinal fluid." Neurosurgery, 50(3): 571-577.

(Continued)

*Primary Examiner* — Oluwatosin A Ogunbiyi
(74) *Attorney, Agent, or Firm* — Tom Hunter; Weaver Austin Villeneuve & Sampson LLP

(57) ABSTRACT

In various embodiments devices and methods for the detection and/or quantification of clinically relevant pathogens (e.g., bacteria, fungi, viruses, etc.) are provided. In certain embodiments the device comprises a lateral-flow assay that detects the bacterium at a concentration of less than about $6 \times 10^6$ cells/mL, less than about $3 \times 10^6$ cells/ml, less than about $1 \times 10^6$ CFU/mL, or less than about 50 µg/mL. In certain embodiments the device comprises an aqueous two-phase system (ATPS) comprising a mixed phase solution that separates into a first phase solution and a second phase solution; and a lateral-flow assay (LFA). In certain embodiments the device comprises a flow-through system comprising a concentration component comprising an aqueous two-phase system (ATPS) comprising a mixed phase solution that separates into a first phase solution and a second phase solution; and a detection component disposed beneath said concentration component.

19 Claims, 15 Drawing Sheets

(56) References Cited

U.S. PATENT DOCUMENTS

| | | |
|---|---|---|
| 9,207,236 B2 | 12/2015 | Cary |
| 9,250,236 B2 | 2/2016 | Babu et al. |
| 9,347,955 B2 | 5/2016 | Pieribone |
| 9,823,247 B2 | 11/2017 | Kamei et al. |
| 10,006,911 B2 | 6/2018 | Kamei et al. |
| 10,359,423 B2 | 7/2019 | Kamei et al. |
| 10,578,616 B2 | 3/2020 | Kamei et al. |
| 11,209,427 B2 | 12/2021 | Kamei et al. |
| 11,287,426 B2 | 3/2022 | Kamei et al. |
| 11,327,075 B2 | 5/2022 | Kamei et al. |
| 11,635,432 B2 | 4/2023 | Kamei et al. |
| 2003/0215358 A1 | 11/2003 | Schulman et al. |
| 2004/0002168 A1 | 1/2004 | Remington et al. |
| 2004/0203079 A1 | 10/2004 | Pentyala |
| 2004/0214171 A1 | 10/2004 | Yamashita et al. |
| 2004/0241752 A1 | 12/2004 | Anderson et al. |
| 2005/0239216 A1 | 10/2005 | Feistel |
| 2006/0019406 A1 | 1/2006 | Wei et al. |
| 2006/0025579 A1 | 2/2006 | Riedl et al. |
| 2007/0003992 A1 | 1/2007 | Pentyala |
| 2007/0140911 A1 | 6/2007 | Carney et al. |
| 2007/0196864 A1 | 8/2007 | Pentyala |
| 2007/0292902 A1 | 12/2007 | Cheng et al. |
| 2008/0081341 A1 | 4/2008 | Maher et al. |
| 2008/0138842 A1 | 6/2008 | Boehringer et al. |
| 2008/0227113 A1 | 9/2008 | Pentyala |
| 2008/0227220 A1 | 9/2008 | Franse et al. |
| 2008/0254440 A1 | 10/2008 | Uchida et al. |
| 2009/0110601 A1 | 4/2009 | Levi et al. |
| 2009/0191648 A1 | 7/2009 | Bohannon |
| 2010/0227323 A1 | 9/2010 | Baeumner et al. |
| 2011/0003310 A1 | 1/2011 | Ennis et al. |
| 2011/0072885 A1 | 3/2011 | Inana et al. |
| 2011/0151479 A1 | 6/2011 | Stevens et al. |
| 2011/0312074 A1 | 12/2011 | Azimi et al. |
| 2012/0107956 A1 | 5/2012 | Boehringer et al. |
| 2012/0238008 A1 | 9/2012 | Henry et al. |
| 2013/0065784 A1 | 3/2013 | Takayama et al. |
| 2013/0102063 A1 | 4/2013 | Levi et al. |
| 2013/0266956 A1 | 10/2013 | Tia et al. |
| 2013/0280693 A1 | 10/2013 | Mace et al. |
| 2014/0004539 A1 | 1/2014 | Simon et al. |
| 2014/0038222 A1 | 2/2014 | Alt et al. |
| 2014/0228549 A1 | 8/2014 | Schembecker |
| 2015/0017656 A1 | 1/2015 | Wang |
| 2015/0099656 A1 | 4/2015 | Manuguerra et al. |
| 2015/0198592 A1 | 7/2015 | Wang |
| 2015/0253320 A1 | 9/2015 | Kamei et al. |
| 2015/0323534 A1 | 11/2015 | Egan et al. |
| 2016/0266119 A1 | 9/2016 | Sambursky et al. |
| 2016/0282343 A1 | 9/2016 | Jeyendran et al. |
| 2016/0313307 A1 | 10/2016 | Titmus et al. |
| 2016/0334397 A1 | 11/2016 | Yan et al. |
| 2017/0323441 A1 | 11/2017 | Shah et al. |
| 2018/0100854 A1 | 4/2018 | Kamei et al. |
| 2018/0188256 A1 | 7/2018 | Wong |
| 2018/0259521 A1 | 9/2018 | Kamei et al. |
| 2019/0004057 A1 | 1/2019 | Kwon et al. |
| 2019/0033308 A1 | 1/2019 | Kamei et al. |
| 2019/0187140 A1 | 6/2019 | Kamei et al. |
| 2019/0250156 A1 | 8/2019 | Kamei et al. |
| 2019/0391143 A1 | 12/2019 | Kamei et al. |
| 2020/0033336 A1 | 1/2020 | Kamei et al. |
| 2020/0124595 A1 | 4/2020 | Irudayaraj et al. |
| 2020/0150116 A1 | 5/2020 | Kamei et al. |
| 2020/0284791 A1 | 9/2020 | Kamei et al. |
| 2022/0146507 A1 | 5/2022 | Kamei et al. |

FOREIGN PATENT DOCUMENTS

| | | | |
|---|---|---|---|
| CN | 103008038 A | 4/2013 | |
| CN | 106662582 A | 5/2017 | |
| EP | 1064553 A1 | 1/2001 | |
| EP | 1340085 A1 | 9/2003 | |
| EP | 1436592 A1 | 7/2004 | |
| EP | 1733233 A2 | 12/2006 | |
| EP | 1771734 A1 | 4/2007 | |
| EP | 0941468 B1 | 7/2007 | |
| EP | 2076775 A2 | 7/2009 | |
| EP | 2126569 A2 | 12/2009 | |
| EP | 2245135 A2 | 11/2010 | |
| EP | 2426498 A1 | 3/2012 | |
| ES | 2382381 T3 * | 6/2012 | ......... A61B 10/0045 |
| JP | H03130663 A | 6/1991 | |
| JP | 2003250575 A | 9/2003 | |
| JP | 2007500363 A | 1/2007 | |
| JP | 2008537119 A | 9/2008 | |
| JP | 2011075366 A | 4/2011 | |
| JP | 2013531259 A | 8/2013 | |
| JP | 2013181870 A | 9/2013 | |
| KR | 20080103200 A | 11/2008 | |
| WO | WO-9818964 A1 | 5/1998 | |
| WO | WO-2004081528 A2 | 9/2004 | |
| WO | WO-2005042579 A1 | 5/2005 | |
| WO | WO-2005074609 A2 | 8/2005 | |
| WO | WO-2005098439 A2 | 10/2005 | |
| WO | WO-2007092302 A2 | 8/2007 | |
| WO | WO-2008043040 A2 | 4/2008 | |
| WO | WO-2011116256 A2 | 9/2011 | |
| WO | WO-2011159537 A2 | 12/2011 | |
| WO | WO-2012010666 A1 | 1/2012 | |
| WO | WO-2013105090 A1 | 7/2013 | |
| WO | WO-2015134938 A1 | 9/2015 | |
| WO | WO-2017041030 A1 | 3/2017 | |
| WO | WO-2017214315 A1 | 12/2017 | |
| WO | WO-2018039139 A1 | 3/2018 | |
| WO | WO-2018183211 A1 | 10/2018 | |
| WO | WO-2018222765 A1 | 12/2018 | |

OTHER PUBLICATIONS

Carter and Cary (2007) "Lateral flow microarrays: a novel platform for rapid nucleic acid detection based on miniaturized lateral flow chromatography," Nucleic Acids Research 35(10): e74 (11 pages).

Center for Disease Control and Prevention. Diagnostic Tests for Zika Virus. "Updated Guidance for US Laboratories Testing for Zika Virus Infection Jul. 24, 2017"; Availabe at: https://www.cdc.gov/zika/transmission/index.html, 16 pages.

Chiu, et al. (2010) "Generation of Porous Poly(Ethylene Glycol) Hydrogels by Salt Leaching." Tissue Engineering Part C: Methods 16: 905-912.

Chiu et al. (2014) "Biomarker concentration and detection directly on paper," abstract, MicroTAS Annual Meeting, San Antonio, Texas, 3 pages.

Chiu et al. (2014) "Dextran-coated gold nanoprobes for the concentration and detection of protein biomarkers," Annals of Biomedical Engineering 42(11): 2322-2332.

Chiu et al. (2014) "Simultaneous concentration and detection of biomarkers on paper," Lab Chip 14: 3021-3028.

Chiu et al. (2014) "Simultaneous concentration and detection of biomarkers on paper," poster presentation, MicroTAS Annual Meeting, San Antonio, Texas, 1 page.

Chiu et al. (2014) "Simultaneously concentrating and detecting biomarkers on paper," abstract of podium presentation, The Biomedical Engineering Society Annual Meeting, San Antonio, Texas, 1 page.

Chiu et al. (2014) "Simultaneously concentrating and detecting biomarkers on paper," slides from podium presentation, The Biomedical Engineering Society Annual Meeting, San Antonio, Texas, 52 slides.

Chiu et al. (2014) "Manipulating gold nanoparticles to achieve effective and rapid detection of protein biomarkers for resource-poor settings," slides from presentation, not published/distributed. The Annual UC System wide Bioengineering Symposium, Irvine, California, 24 slides.

Chiu et al. (2014) "Polymer-coated gold nanoprobes for the concentration and detection of protein biomarkers for resource-poor settings," The Biomedical Engineering Society Annual Meeting, San Antonio, Texas, poster, 1 page.

(56) References Cited

OTHER PUBLICATIONS

Chiu et al. (2014) "Polymer-coated gold nanoprobes for the concentration and detection of protein biomarkers for resource-poor settings," The Biomedical Engineering Society Annual Meeting, San Antonio, Texas, published abstract, 1 page.
Chiu et al., (2015) "An aqueous two-phase system for the concentration and extraction of proteins from the interface for detection using the lateral-flow immunoassay," PLoS One 10: e0142654 (14 pages).
Chiu et al. (2015) "Creating the gold standard point-of-care test for sexually transmitted infections," 20 slide deck, not published, not distributed, for judging only, OneStart Competition, 20 pages.
Chiu et al. (2015) "Creating the gold standard point-of-care test for sexually transmitted infections," 3 minute/3 slide deck, OneStart Competition, 3 pages.
Cho, et al. (2013) "Lateral-flow enzyme immunoconcentration for rapid detection of Listeria monocytogenes." Anal Bioanal Chem 405:3313-3319.
CN First Office Action dated Jan. 22, 2018 issued in CN 201580023439.9.
CN First Office Action dated Mar. 27, 2020 issued in CN 201680059385.6.
CN Fourth Office Action dated Mar. 24, 2022 issued in CN 201680059385.6 with English translation.
CN Office Action dated Feb. 24, 2022, in Application No. CN201780046652 with English translation.
CN Second Office Action dated Feb. 20, 2021 issued in CN 201680059385.6.
CN Second Office Action dated Nov. 29, 2018 issued in CN 201580023439.9.
CN Third Office Action dated Jun. 22, 2021 issued in CN 201680059385.6.
EP 2nd Office Action dated Jul. 27, 2021 issued in EP 17810966.6.
EP Extended Search Report dated Mar. 23, 2021 issued in EP 20200335.6.
EP Extended Search Report dated Oct. 26, 2017 issued in EP 15758881.5.
EP Extended Supplementary Search Report dated Dec. 6, 2019 issued in EP 17810966.6.
EP Extended Supplementary Search Report dated Jan. 27, 2021 issued in EP 18809609.3.
EP Extended Supplementary Search Report dated Jun. 14, 2019 issued in EP 16843134.4.
EP Office Action dated Oct. 6, 2020 issued in EP 17810966.6.
EP Partial Supplementary Search Report dated Feb. 4, 2019 issued in EP 16843134.4.
Fang et al. (2011) "Barcode lateral flow immunochromatographic strip for prostate acid phosphatase determination," J. Pharmaceut. Biomed. Anal., 56(5): 1035-1040.
Fu et al. (2011) "Enhanced sensitivity of lateral flow tests using a two-dimensional paper network format," Anal. Chem. 83(20): 7941-7946 (NIH Public Access—Author Manuscript—12 pages).
Fung et al. (2009) "Development of a creatinine enzyme-based bar-code-style lateral-flow assay," Analytical and Bioanalytical Chemistry, 393(4): 1281-1287.
Fung et al. (2009) "Development of enzyme-based bar code-style lateral-flow assay for hydrogen peroxide determination," Anal Chim Acta. 634(1): 89-95.
GCA Saliva-Check Mutans product sheet. 2011. http://www.gcamerica.com/storage/dps_c/GCA_SALIVA-CHECK_MUTANS-iPad.pdf retrieved Sep. 21, 2019.
International Search Report and Written Opinion dated Nov. 30, 2021, in PCT Application No. PCT/US2021/046166.
JP 2nd Office Action dated Aug. 30, 2021 issued in JP 2018-511707.
JP 2nd Office Action dated Feb. 3, 2020 issued in JP 2016-573716.
JP Office Action dated Feb. 14, 2022, in Application No. JP2021-15690 with English translation.
JP Office Action dated Feb. 8, 2019 issued in JP 2016-573716.
JP Office Action dated Mar. 7, 2022, in Application No. JP2018-564267 with English translation.
JP Office Action dated May 17, 2021 issued in JP 2018-564267.
JP Office Action dated Sep. 7, 2020 issued in JP 2018-511707.
Jue et al. (2014) "Simultaneous Concentration and Detection of Biomarkers on Paper," published document for the Capstone Design team, MicroTAS Annual Meeting, San Antonio, Texas, 7 pages.
Jue et al. (2014) "Using an aqueous two-phase polymer-salt system to rapidly concentrate viruses for improving the detection limit of the lateral-flow immunoassay," Biotechnology and Bioengineering 111(12): 2499-2507.
Jue et al. "Simultaneous Concentration and Detection of Biomarkers on Paper," document submitted but not published, UCLA, 23 pages.
Kim, et al. (2013) "Image Analysis of a Lateral Flow Strip Sensor for the Detection of *Escherichia coli* 0157:H7." J. of Biosystems Eng. 38(4):335-340.
Koczula, et al. (2016) "Lateral flow assays." Essays in Biochemistry 60: 111-120.
KR Office Action dated Aug. 23, 2021 issued in KR 10-2019-7000413.
KR Office Action dated Jan. 25, 2022, in Application No. KR1020167027705 with English translation.
KR Office Action dated Mar. 22, 2021 issued in KR 10-2016-7027705.
Leung et al. (2008) "InfectCheck CRP barcode-style lateral flow assay for semi-quantitative detection of C-reactive protein in distinguishing between bacterial and viral infections," J Immunol Meth. 336(1): 30-36.
Luo, et al. (2005) "PDMS microfludic device for optical detection of protein immunoassay using gold nanoparticles." Lab on a Chip 5:726-729.
Mashayekhi et al. (2009) "Concentration of mammalian genomic DNA using two-phase aqueous micellar systems," Biotechnology and Bioengineering 102(6): 1613-1623, publ online Nov. 3, 2008, publ in journal Apr. 15, 2009.
Mashayekhi et al. (2012) "Enhancing the lateral-flow immunoassay for detection of proteins using an aqueous two-phase micellar system," Anal. Bioanal. Chem. 404: 2057-2066.
Mashayekhi F., et al., "Enhancing the Lateral-flow Immunoassay for Viral Detection Using an Aqueous Two-phase Micellar System", Analytical and Bioanalytical Chemistry, (Sep. 24, 2010), vol. 398, No. 7, pp. 2955-2961.
McCudden et al. (2012) "Evaluation of high resolution gel beta 2-transferrin for detection of cerebrospinal fluid leak," Clinical Chemistry and Laboratory Medicine 6 pages [Abastract].
McCudden et al. (2013) "Evaluation of high resolution gel β2-transferrin for detection of cerebrospinal fluid leak." Clin. Chem. Lab. Med., 51(2): 311-315, CCLM / FESCC. 0. 1-5. 10.1515/cclm-2012-0408.
Mosley G. et al. (2017) "Improved lateral-flow immunoassays for chlamydia and immunoglobulin M by sequential rehydration of two-phase system components within a paper-based diagnostic" Mikrochimica Acta 184(10): 4055-4064.
MY Office Action dated Dec. 2, 2019 issued in MY PI2016001615.
NIH Small Business Technology Transfer Grant Application, Proposal to improve healthcare of tooth decay by developing a point-of-care (POC) diagnostic device, 6 pages, submitted Nov. 19, 2014.
PCT International Preliminary Report on Patentability dated Dec. 20, 2018 issued in PCT/US2017/036418.
PCT International Preliminary Report on Patentability dated Dec. 3, 2019 issued in PCT/US2018/035204.
PCT International Preliminary Report on Patentability dated Feb. 26, 2019 issued in PCT/US2017/047849.
PCT International Preliminary Report on Patentability dated Mar. 15, 2018 issued in PCT/US2016/050257.
PCT International Preliminary Report on Patentability dated Oct. 1, 2019 issued in PCT/US2018/024392.
PCT International Preliminary Report on Patentability dated Sep. 13, 2016 issued in PCT/US2015/019297.
PCT International Search Report and Written Opinion dated Aug. 3, 2018 issued in PCT/US2018/035204.
PCT International Search Report and Written Opinion dated Dec. 1, 2017 issued in PCT/US2017/047849.

(56) References Cited

OTHER PUBLICATIONS

PCT International Search Report and Written Opinion dated Dec. 22, 2016 issued in PCT/US2016/050257.
PCT International Search Report and Written Opinion dated Jun. 15, 2018 issued in PCT/US2018/024392.
PCT International Search Report and Written Opinion dated Jun. 3, 2015 issued in PCT/US2015/019297.
PCT International Search Report and Written Opinion dated Sep. 20, 2017 issued in PCT/US2017/036418.
Pereira et al. (2014) "Enhancing the phase separation behavior of a micellar aqueous two-phase system in a paper-based diagnostic," The Annual UC System wide Bioengineering Symposium, Irvine, California, poster, 1 page.
Pereira et al. (2014) "Enhancing the phase separation behavior of a micellar aqueous two-phase system in a paper-based diagnostic," UC Bioengineering Symposium 2014, Abstract, 2 pages.
Pereira et al. (2014) "Paper-based diagnostic accelerates phase separation of a micellar aqueous two-phase system," The Biomedical Engineering Society Annual Meeting, San Antonio, Texas, poster, 1 page.
Pereira et al. (2015) "Improving malaria biomarker detection and accelerating micellar two-phase separation with a paper-based diagnostic," Department of Engineering, UCLA 90095, UCLA Tech Forum, abstract, 1 page.
Pereira et al. (2015) "Improving malaria biomarker detection and accelerating micellar two-phase separation with a paper-based diagnostic," The UCLA Engineering Tech Forum, Los Angeles, California, poster, 1 page.
Pereira et al. (2015) "Single-step, paper-based concentration and detection of a malaria biomarker," Analytica Chimica Acta 882: 83-89.
Pereira et al. "Paper-based diagnostic accelerates phase separation of a micellar aqueous two-phase system," Department of Engineering, University of California, Los Angeles, abstract, 2 pages.
Phase Diagnostics, Business Plan, OneStart Competition 2015, May 2015, 12 pages.
Raja, S. et al., "Aqueous Two Phase Systems for the Recovery of Biomolecules—A Review", Science and Technology, 2011, vol. 1, No. 1, pp. 7-16.
Risch, et al. (2005) "Rapid, accurate and non-invasive detection of cerebrospinal fluid leakage using combined determination of β-trace protein in secretion and serum" Clinica Chimica Acta 351: 169-176.
Sampaio et al. (2009) "Predictability of quantification of beta-trace protein for diagnosis of cerebrospinal fluid leak: Cutoff determination in nasal fluids with two control groups." Am. J. Rhinol. Allerg. 23(6): 585-590.
Sarangi, B.K. et al., "Purification of Alkaline Protease from Chicken Intestine by Aqueous Two Phase System of Polyethylene Glycol and Sodium Citrate", Journal of Food Science and Technology, Nov. 1, 2010, vol. 48, No. 1, pp. 36-44.
SG Examination Report dated May 14, 2019 issued in SG 11201607582R.
SG Office Action [Search Report and Written Opinion] dated Jan. 24, 2018 issued in SG 11201607582R.
Song, et al. (2016) "Instrument-Free Point-of-Care Molecular Detection of Zika Virus." Analytical Chemistry 88: 7289-7294.
U.S. Final Office Action dated Jun. 1, 2021 issued in U.S. Appl. No. 15/756,542.
U.S. Final Office Action dated Jun. 4, 2020 issued in U.S. Appl. No. 15/756,542.
U.S. Final Office Action dated May 17, 2021 issued in U.S. Appl. No. 16/498,312.
U.S. Notice of Allowance dated Apr. 3, 2019 issued in U.S. Appl. No. 15/990,398.
U.S. Notice of Allowance dated Aug. 23, 2021 issued in U.S. Appl. No. 16/498,312.
U.S. Notice of Allowance dated Aug. 8, 2017 issued in U.S. Appl. No. 14/641,022.
U.S. Notice of Allowance dated Feb. 28, 2018 issued in U.S. Appl. No. 15/787,638.
U.S. Notice of Allowance dated Jan. 12, 2022, in U.S. Appl. No. 16/326,687.
U.S. Notice of Allowance dated Jul. 20, 2017 issued in U.S. Appl. No. 14/641,022.
U.S. Notice of Allowance dated Nov. 16, 2021 issued in U.S. Appl. No. 15/756,542.
U.S. Office Action Advisory Action dated Aug. 20, 2021 issued in U.S. Appl. No. 15/756,542.
U.S. Office Action Advisory Action (second) dated Sep. 17, 2021 issued in U.S. Appl. No. 15/756,542.
U.S. Office Action dated Jan. 21, 2021 issued in U.S. Appl. No. 15/756,542.
U.S. Office Action dated Jan. 6, 2017 issued in U.S. Appl. No. 14/641,022.
U.S. Office Action dated Jun. 4, 2021 issued in U.S. Appl. No. 16/326,687.
U.S. Office Action dated Jun. 9, 2021 issued in U.S. Appl. No. 16/307,125.
U.S. Office Action dated Nov. 2, 2018 issued in U.S. Appl. No. 15/990,398.
U.S. Office Action dated Oct. 27, 2020 issued in U.S. Appl. No. 16/498,312.
U.S. Office Action dated Sep. 26, 2019 issued in U.S. Appl. No. 15/756,542.
U.S. Office Action [Restriction Requirement] dated May 14, 2019 issued in U.S. Appl. No. 15/756,542.
U.S. Restriction Requirement dated Jan. 25, 2022, in U.S. Appl. No. 16/616,923.
Wong et al. (2015) "Direct Reading of Bona Fide Barcode Assays for Diagnostics with Smartphone Apps," Scientific Reports 5, Article No. 11727 (11 pages).
Wu et al. (Jul. 21, 2014) "Research highlights: increasing paper possibilities" Lab on a Chip, 14(17) 3258-3261.
Yu, et al. (2009) "Flow-through functionalized PDMS microfluidic channels with dextran derivative for ELISAs." Lab on a Chip 9:1243-1247.
AU Office Action dated Aug. 8, 2023, in application No. AU2017277631.
AU Office Action dated Oct. 10, 2022, in Application No. AU2016318103.
Bernasconi, L., et al., "Retrospective Validation of a Beta-trace Protein Interpretation Algorithm for the Diagnosis of Cerebrospinal Fluid Leakage", Clinical Chemistry and Laboratory Medicine, published online Sep. 22, 2016, vol. 55, No. 4, pp. 554-560.
CA Office Action dated Jan. 28, 2023, in Application No. CA3002020.
CA Office Action dated May 19, 2022, in Application No. CA3002020.
CN Office Action dated Aug. 29, 2022 in Application No. CN201780046652 with English translation.
CN Office Action dated Dec. 15, 2022 in Application No. 201880042214.1 with English translation.
CN Office Action dated Oct. 25, 2022, in application No. CN201911106057.9 with English translation.
European Office Action dated Mar. 9, 2023 in Application No. EP18809609.3.
International Preliminary Report on Patentability dated Mar. 2, 2023, in PCT Application No. PCT/US2021/046166.
JP Office Action dated Apr. 3, 2023 in Application No. JP2022-28070 with English translation.
JP Office Action dated Aug. 8, 2022, in Application No. JP2021-15690 with English translation.
JP Office Action dated Dec. 12, 2022, in Application No. 2018-564267 with English translation.
KR Office Action dated Apr. 26, 2023, in Application No. KR10-2019-7000413 with English translation.
KR Office Action dated Aug. 10, 2023, in Application No. KR10-2019-7000413 with English translation.
KR Office Action dated Jan. 26, 2023, in Application No. KR10-2018-7009424 with English translation.
KR Office Action dated Jun. 21, 2022, in Application No. KR10-2019-7000413 with English translation.
Le, A.M., et al., "Improving the Lateral-Flow Immunoassay Using Aqueous Two-Phase Systems", 2012, pp. 78 pages.

(56) References Cited

OTHER PUBLICATIONS

Ribeiro S.C., et al., "Isolation of Plasmid Dna From Cell Lysates by Aqueous Two-phase Systems," Biotechnology and Bioengineering, May 2002, vol. 78(4), pp. 376-384.
U.S. Final office Action dated Jun. 23, 2022 in U.S. Appl. No. 16/307,125.
U.S. Final Office Action dated Mar. 10, 2023 in U.S. Appl. No. 16/616,923.
U.S. Non-Final office Action dated Apr. 17, 2023 in U.S. Appl. No. 17/530,336.
U.S. Non-Final Office Action dated Jun. 24, 2022, in U.S. Appl. No. 16/616,923.
U.S. Non-Final Office Action dated May 25, 2022, in U.S. Appl. No. 16/751,114.
U.S. Notice of Allowance dated Aug. 23, 2023 in U.S. Appl. No. 17/530,336.
U.S. Notice of Allowance dated Dec. 13, 2022 in U.S. Appl. No. 16/751,114.
U.S. Notice of Allowance dated Jul. 19, 2023, in U.S. Appl. No. 16/307,125.
U.S. Appl. No. 18/120,329, inventors Kamei et al., filed Mar. 10, 2023.

\* cited by examiner

METHODS AND DEVICES FOR ANALYTE COLLECTION, EXTRACTION, CONCENTRATION, AND DETECTION FOR CLINICAL APPLICATIONS

CROSS-REFERENCE TO RELATED APPLICATIONS

This application is a divisional of U.S. Ser. No. 15/756,542, filed on Feb. 28, 2018, now U.S. Pat. No. 11,287,426 issued on Mar. 29, 2022 which is a U.S. 371 National Phase of PCT/US2016/050257, filed on Sep. 2, 2016, which claims benefit of and priority to U.S. Ser. No. 62/214,801, filed on Sep. 4, 2015, each of which is incorporated herein by reference in its entirety for all purposes.

STATEMENT OF GOVERNMENTAL SUPPORT

[Not Applicable]

BACKGROUND

Assays have been used to detect the presence or the concentration of various substances or pathogens in biological fluids. In a solid phase immunoassay, a receptor, typically an antibody which is specific for the ligand to be detected, is immobilized on a solid support. A test fluid that may comprise the analyte to be detected is contacted with the solid support and a receptor-analyte pair is formed when the target analyte is present. In order to make the receptor-ligand pair visible, labeled antibodies may be used that bind to the receptor-ligand pair followed by visual detection of the labeled antibody bound to the receptor-ligand pair.

In so-called sandwich immunoassays, the analyte is typically sandwiched between a labeled antibody and an antibody immobilized on a solid support.

Porous materials such as nitrocellulose, nylon, cellulose acetate, glass fibers and other porous polymers have been employed as solid supports in solid phase immunoassays. In so-called lateral-flow assays, a fluid wherein the analyte is to be detected is applied to one end of a porous membrane layer and flows in lateral direction through the membrane under the action of capillary forces to be captured by an immobilized "receptor" that is capable of binding the analyte to be detected.

A general issue with lateral-flow immunoassays is assay sensitivity and therewith signal intensity.

SUMMARY

In various embodiments devices and methods for the detection and/or quantification of clinically relevant pathogens (e.g., bacteria, fungi, viruses, etc.) are provided. In certain embodiments the device comprises a lateral-flow assay that detects the bacterium at a concentration of less than about $6 \times 10^6$ cells/mL, less than about $3 \times 10^6$ cells/ml, less than about $1 \times 10^6$ CFU/mL, or less than about 50 µg/mL. In certain embodiments the device comprise an aqueous two-phase system (ATPS) comprising a mixed phase solution that separates into a first phase solution and a second phase solution; and a lateral-flow assay (LFA). In certain embodiments the device comprises a flow-through system comprising: a concentration component comprising an aqueous two-phase system (ATPS) comprising a mixed phase solution that separates into a first phase solution and a second phase solution; and a detection component disposed beneath said concentration component.

Various embodiments contemplated herein may include, but need not be limited to, one or more of the following:

Embodiment 1: A device for the detection and/or quantification of a bacterium, a fungus, or a virus in a sample, the device comprising a lateral-flow assay that detects the bacterium at a concentration of less than about $6 \times 10^6$ cells/mL, less than about $3 \times 10^6$ cells/ml, less than about $1 \times 10^6$ CFU/mL, or less than about 50 µg/mL.

Embodiment 2: A device for the detection and/or quantification of a bacterium, a fungus, or a virus in a sample, said device comprising an aqueous two-phase system (ATPS) comprising a mixed phase solution that separates into a first phase solution and a second phase solution; and a lateral-flow assay (LFA).

Embodiment 3: The device of embodiment 2, wherein the LFA comprises a porous matrix that is configured to receive and/or contain an ATPS or components thereof.

Embodiment 4: The device according to any one of embodiments 2-3, wherein said LFA comprises a conjugate pad, a test line comprising an antibody that binds said bacterium, a control line comprising a secondary antibody, optionally an absorbent pad, and optionally a sample pad.

Embodiment 5: A device for the detection and/or quantification of a bacterium, a fungus, or a virus in a sample, said device comprising: a flow-through system comprising:
 a concentration component comprising an aqueous two-phase system (ATPS) comprising a mixed phase solution that separates into a first phase solution and a second phase solution; and
 a detection component disposed beneath said concentration component.

Embodiment 6: The device of embodiment 5, wherein said concentration component comprises one or more layers of a paper.

Embodiment 7: The device according to any one of embodiments 5-6, wherein said detection component comprises a conjugate pad, a reaction pad, and optionally a sink.

Embodiment 8: The device according to any one of embodiments 1-7, wherein said LFA or said flow-through system detects said bacterium in less than about 10 minutes.

Embodiment 9: The device according to any one of embodiments 1-8, wherein said device is configured for the detection of a bacterium.

Embodiment 10: The device of embodiment 9, wherein said bacterium is an oral bacterium, a bacterium found in urine, a bacterium found in vaginal fluid, or a bacterium found on a vaginal swab, or a bacterium found on an endocervical swab.

Embodiment 11: The device of embodiment 10, wherein said bacterium is an oral bacterium.

Embodiment 12: The device of embodiment 11, wherein said oral bacterium comprises *Prevotella* sp. (e.g., *Pr. intermedia, Pr. nigrescens*, etc.), *Porphyromonas* sp. (e.g., *Porph. gingivalis*, etc.), *Streptococcus* sp. (e.g., *S. mutans*, etc.), *Actinomyces viscosus, Lactobacillus casei, Staphylococcus aureus, Coandica albicans, Lactobacillus acidophilus, Capnacytophaga gingivalis, Fusobacteriun nucleatum*, or *Bacteroides fortsythus*.

Embodiment 13: The device of embodiment 10, wherein said bacterium is a bacterium found in vaginal fluid.

Embodiment 14: The device of embodiment 13, wherein said bacterium comprises *Trichomonas* sp., *Actinomyces* sp., *Gardnerella* sp., *Neisseria* sp., *Chlamydia* sp., or *Treponema* sp.

Embodiment 15: The device of embodiment 10, wherein said bacterium is a bacterium found in urine.

Embodiment 16: The device of embodiment 15, wherein said bacterium comprises *E. coli*, *Proteus* sp., *Trichomonas* sp., *Actinomyces* sp., *Gardnerella* sp., *Neisseria* sp., *Chlamydia* sp., or *Treponema* sp.

Embodiment 17: The device according to any one of embodiments 11-12, wherein the LFA or the detection component comprises an antibody that detects *S. mutans*.

Embodiment 18: The device according to any one of embodiments 1-17, wherein said ATPS is combined with said sample before application to said device.

Embodiment 19: The device according to any one of embodiments 1-17, wherein said ATPS is dehydrated on the lateral-flow assay or in the concentration component of the flow-through assay before the device is contacted with the sample.

Embodiment 20: The device according to any one of embodiments 1-19, wherein the ATPS comprises a mixed phase solution that separates into a first phase solution and a second phase solution after the device is contacted with the sample.

Embodiment 21: The device according to any one of embodiments 1-20, wherein the ATPS comprises a micellar/surfactant solution.

Embodiment 22: The device of embodiment 21, wherein the first phase solution is concentrated in surfactant and the second phase solution has a low concentration of surfactant.

Embodiment 23: The device according to any one of embodiments 1-20, wherein the first phase solution comprises a polymer and the second phase solution comprises a surfactant.

Embodiment 24: The device of embodiment 23, wherein said polymer comprises dextran.

Embodiment 25: The device according to any one of embodiments 23-24, wherein the surfactant comprises a non-ionic surfactant or an alkylpolyglycolether surfactant.

Embodiment 26: The device according to any one of embodiments 23-24, wherein the surfactant comprises a non-ionic surfactant nonionic surfactant that has a hydrophilic polyethylene oxide chain and an aromatic hydrocarbon lipophilic or hydrophobic group (e.g., a Triton-X surfactant).

Embodiment 27: The device according to any one of embodiments 1-20, wherein the first phase solution comprises a first polymer and the second phase solution comprises a second polymer.

Embodiment 28: The device of embodiment 27, wherein the first/second polymer comprises polyethylene glycol, polypropylene glycol, or dextran.

Embodiment 29: The device according to any one of embodiments 1-20, wherein the first phase solution comprises a polymer and the second phase solution comprises a salt.

Embodiment 30: The device of embodiment 29, wherein the first phase solution comprises polyethylene glycol.

Embodiment 31: The device of embodiment 29, wherein the first phase solution comprises polypropylene glycol.

Embodiment 32: The device according to any one of embodiments 29-31, wherein said salt comprises potassium phosphate, sodium sulfate, magnesium sulfate, ammonium sulfate, or sodium citrate.

Embodiment 33: The device according to any one of embodiments 29-31, wherein said salt is potassium phosphate.

Embodiment 34: The device according to any one of embodiments 2-20, wherein the first phase solution comprises a Component 1 of Table 1 and the second phase solution comprises a Component 2 of Table 1.

Embodiment 35: The device according to any one of embodiments 1-34, wherein said device further comprises a probe that interacts with the target bacterium, fungus, or virus.

Embodiment 36: The device of embodiment 35, wherein the device comprises one or more probes that interact with at least 1 target bacteria, fungi or virus, or at least two different target bacteria, fungi or virus, or at least 3 different target bacteria, fungi or virus, or at least 4 different target bacteria, fungi or virus, or at least 5 different target bacteria, fungi or virus, or at least 7 different target bacteria, fungi or virus, or at least 10 different target bacteria, fungi or virus, or at least 15 different target bacteria, fungi or virus, or at least 20 different target bacteria, fungi or virus.

Embodiment 37: The device according to any one of embodiments 35-36, wherein the device includes at least two different probes, or at least 3 different probes, or at least 4 different probes, or at least 5 different probes, or at least 7 different probes, or at least 10 different probes, or at least 15 different probes, or at least 20 different probes.

Embodiment 38: The device according to any one of embodiments 35-37, wherein the probe comprises a synthetic polymer, a metal, a mineral, a glass, a quartz, a ceramic, a biological polymer, or a plastic.

Embodiment 39: The device of embodiment 38, wherein the probe comprises polyethylene, polypropylene, cellulose, chitin, nylon, polyoxymethylene, polytetrafluoroethylene, or polyvinyl chloride.

Embodiment 40: The device of embodiment 38, wherein the probe comprises a biological polymer comprises dextran, polypropylene, or polyethylene glycol.

Embodiment 41: The device of embodiment 38, wherein the probe comprises gold, silver, or platinum.

Embodiment 42: The device according to any one of embodiments 38-41, wherein the probe comprises a nanoparticle.

Embodiment 43: The device of embodiment 42, wherein the nanoparticle is a gold nanoparticle.

Embodiment 44: The device according to any one of embodiments 38-43, wherein the probe comprises a coating.

Embodiment 45: The device of embodiment 44, wherein the coating comprises polypropylene glycol or polyethylene glycol.

Embodiment 46: The device of embodiment 44, wherein the coating comprises dextran.

Embodiment 47: The device of embodiment 44, wherein the coating comprises a hydrophilic protein.

Embodiment 48: The device of embodiment 44, wherein the coating comprises serum albumin.

Embodiment 49: The device according to any one of embodiments 44-48, wherein the coating has an affinity for the first phase solution or the second phase solution.

Embodiment 50: The device according to any one of embodiments 35-49, wherein the probe further comprises a binding moiety that binds the target bacterium, fungus or virus.

Embodiment 51: The device of embodiment 50, wherein the binding moiety comprises an antibody, a lectin, a protein, a glycoprotein, a nucleic acid, a small molecule, a polymer, or a lipid.

Embodiment 52: The device of embodiment 50, wherein the binding moiety is an antibody or antibody fragment.

Embodiment 53: The device of embodiment 52, wherein said antibody is an antibody that specifically binds the bacterium, fungus, or virus.

Embodiment 54: The device according to any one of embodiments 1-53, wherein said device further comprises a signal enhancement reagent.

Embodiment 55: The device of embodiment 54, wherein said signal enhancement reagent comprises a substrate that reacts with an enzyme that is decorated on the surface of probe to form a strong visible product.

Embodiment 56: The device of embodiment 55, wherein said signal enhancement comprises a silver ion.

Embodiment 57: The device according to any one of embodiments 1-56, wherein said device is configured to perform a competition assay.

Embodiment 58: The device according to any one of embodiments 1-56, wherein said device is configured to perform a sandwich assay.

Embodiment 59: The device according to any one of embodiments 1-58, wherein said device detects an analyte (e.g., a bacterium) at a concentration of less than about $6 \times 10^6$ cells/mL, or less than about $3 \times 10^6$ cells/ml, or less than about $1 \times 10^5$ cells/mL, less than about $1 \times 10^6$ CFU/mL, or less than about 50 µg/mL.

Embodiment 60: The device according to any one of embodiments 1-59, wherein false positives appear at an analyte concentration of less than about 12 ng/µL, or less than about 10 ng/µL, or less than about 8 ng/µL, or less than about 6 ng/µL, or less than about 4 ng/µL, or less than about 2 ng/µL.

Embodiment 61: A kit for the detection and/or quantification of a bacterium, said kit comprising: a device according to any one of embodiments 1-60; and a collection device for collecting a biological sample.

Embodiment 62: The kit of embodiment 61, wherein said collection device comprises a device for collecting oral fluid.

Embodiment 63: The kit of embodiment 61, wherein said collection device comprises a device for collecting blood.

Embodiment 64: The kit of embodiment 61, wherein said collection device comprises a urine collection device.

Embodiment 65: The kit of embodiment 61, wherein said collection device comprises a device for collecting vaginal fluid or from a vaginal swab or from an endocervical swab.

Embodiment 66: The kit of embodiment 61, wherein said collection device comprises a device for collecting an environmental sample.

Embodiment 67: A method of detecting and/or quantifying a bacterium, fungus, or virus in a sample comprising:
i) applying the sample to the device of any one of embodiments 1-60; and
ii) detecting a presence or absence and/or quantifying the bacterium fungus or virus on the LFA or detection component of the flow-through device.

Embodiment 68: A method of detecting and/or quantifying a bacterium, fungus, or virus in a sample comprising:
i) applying the sample to an aqueous two-phase system (ATPS);
ii) applying the ATPS or component thereof containing the sample to the device any one of embodiments 1-60; and
iii) detecting a presence or absence and/or quantifying the bacterium on the LFA or detection component of the flow-through device.

Embodiment 69: The method according to any one of embodiments 67-68, wherein the sample is an environmental sample, an oral sample, a vaginal fluid sample, a urine sample, a sample from a vaginal swab, or a sample from an endocervical swab.

Embodiment 70: The method of embodiment 69, wherein said sample is a buccal sample, or an oral fluid sample.

Embodiment 72: The method according to any one of embodiments 67-70, wherein false positives appear at an analyte concentration of less than about 12 ng/µL, or less than about 10 ng/µL, or less than about 8 ng/µL, or less than about 6 ng/µL, or less than about 4 ng/µL, or less than about 2 ng/µL.

DETAILED DESCRIPTION

In various embodiments methods and devices are provided for analyte collection, extraction, concentration, and detection for clinical applications. In certain embodiments the devices permit the rapid detection and/or quantification of bacteria, fungi, and viruses in biological samples (e.g., oral, urine, and vaginal samples).

In certain embodiments lateral-flow assay (LFA) devices (see, e.g., FIG. 10) and/or flow-through (spot) assay devices (see, e.g., FIG. 4) are provided that are accurate, sensitive, portable, disposable, and well suited to use at point of care with minimal training or equipment.

In certain embodiments the lateral-flow assay devices or the flow-through assay devices can be used directly with a sample to be assayed. In certain embodiments the lateral-flow assay devices or the flow-through assay devices can be used with a sample in which the target (e.g. target molecule(s), target microorganism(s), etc.) have been concentrated before application to the device, using for example, an aqueous two-phase system (ATPS). In certain embodiments the target (e.g. target molecule(s), target microorganism(s), etc.) are concentrated, using e.g., ATPS, on the device itself.

Concentration of the Target Biomolecules

The concentration of target biomolecules using ATPS can be performed in either a bulk liquid, or as the sample solution flows in, e.g., a lateral-flow assay or a flow-through (spot assay), e.g., in a paper membrane.

Concentration in Liquid ATPS

Figure 1:
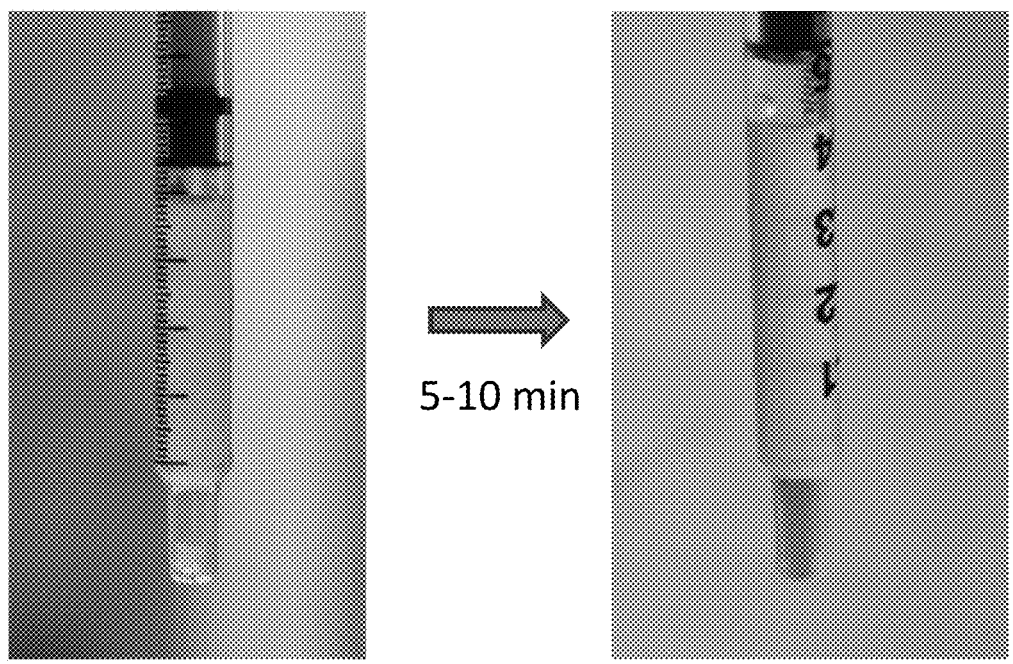
FIG. 1 illustrates rapid target concentration and easy extraction using PPG/salt ATPS in a syringe. Sample containing target biomolecules (purple) is mixed with the ATPS solution. After 5-10 min of incubation at room temperature, the targets are concentrated extremely in the bottom phase, and can be easily extracted and applied to the subsequent detection step by pressing the plunger of the syringe.
Figure 2:
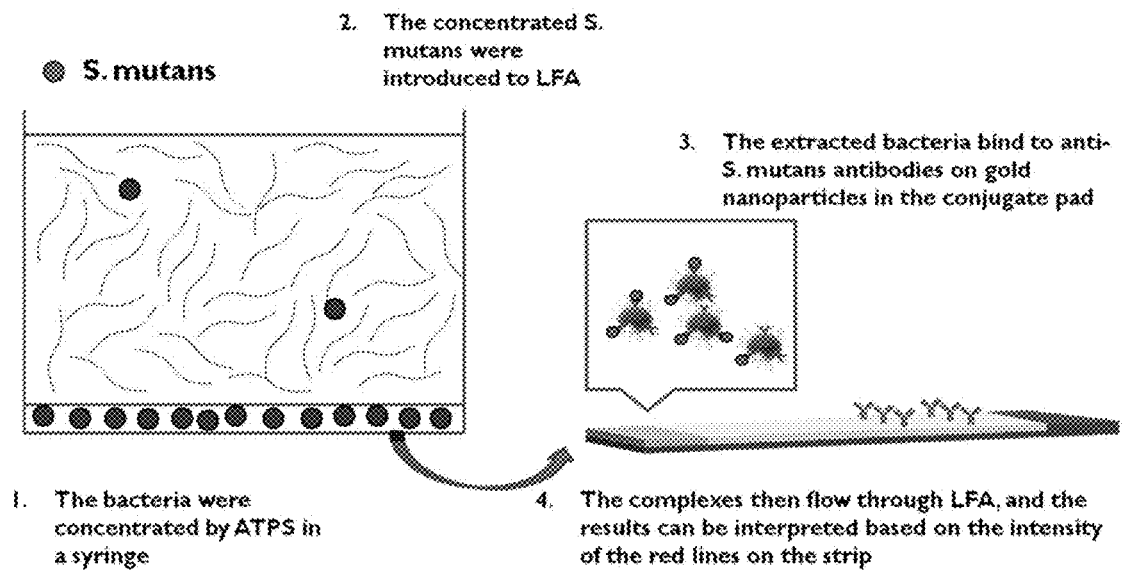
FIG. 2 illustrates an assay where the ATPS containing sample is applied to an assay device (e.g., LFA).

In certain illustrative embodiments a collected sample, (e.g., a tissue sample, a biological fluid such as urine, saliva, and blood, sputum, vaginal fluid, seminal fluid, cerebrospinal fluid, lymph, vaginal swab, endocervical swab, plaque from teeth, and the like), can be combined with a suspending solution (e.g., a buffer) or combined directly with an ATPS solution or directly applied to paper or a suspending solution containing the sample applied to a paper to rehydrate ATPS components that were previously dried onto paper. In some cases, mixing by the user may be required to achieve a well-mixed, homogeneous solution. In various embodiments a polymer/salt, polymer/polymer, micellar/polymer, or micellar ATPS may be used. In one of the examples described below, a polypropylene glycol (PPG):potassium phosphate salt ATPS was used to concentrate Streptococcus mutans (S. mutans) by 60-fold within 10 min (see, e.g., FIG. 1). If the target analyte (e.g., target biomolecule) is large, such as a bacterium, fungus or virus, it will be partitioned, or distributed, extremely into one of the two phases in the ATPS, which can then be introduced to a downstream detection component in the LFA or flow-through assay. In certain embodiments, if the target analyte is small, such as a protein, metabolite, hormone, large probes that are decorated with specific binding moieties can be used to capture the target, and subsequently be concentrated into one of the phases in ATPS for downstream detection. In certain embodiments the phase that contains the concentrated target analyte(s) (e.g., biomolecule(s)) can be introduced to the detection component by physical extraction using a pipette or dropper, or can be introduced via a syringe, e.g., as illustrated in FIG. 1.

Concentration as Fluid Flows on Paper

In various embodiments the concentration step can also be accelerated with paper. For example, the collected specimen can be mixed with ATPS components and introduced to a paper device that can facilitate, enhance, and accelerate phase separation. The target biomolecules can be concentrated in the leading front of the flow on the paper membrane and can seamlessly be introduced to the subsequent detection component.

Alternatively, the ATPS components can be pre-dehydrated onto the paper membranes. In this case, the collected specimen can be directly applied to the paper membrane without pre-mixing with the ATPS components.

Detection of Target Biomolecules

Figure 3:
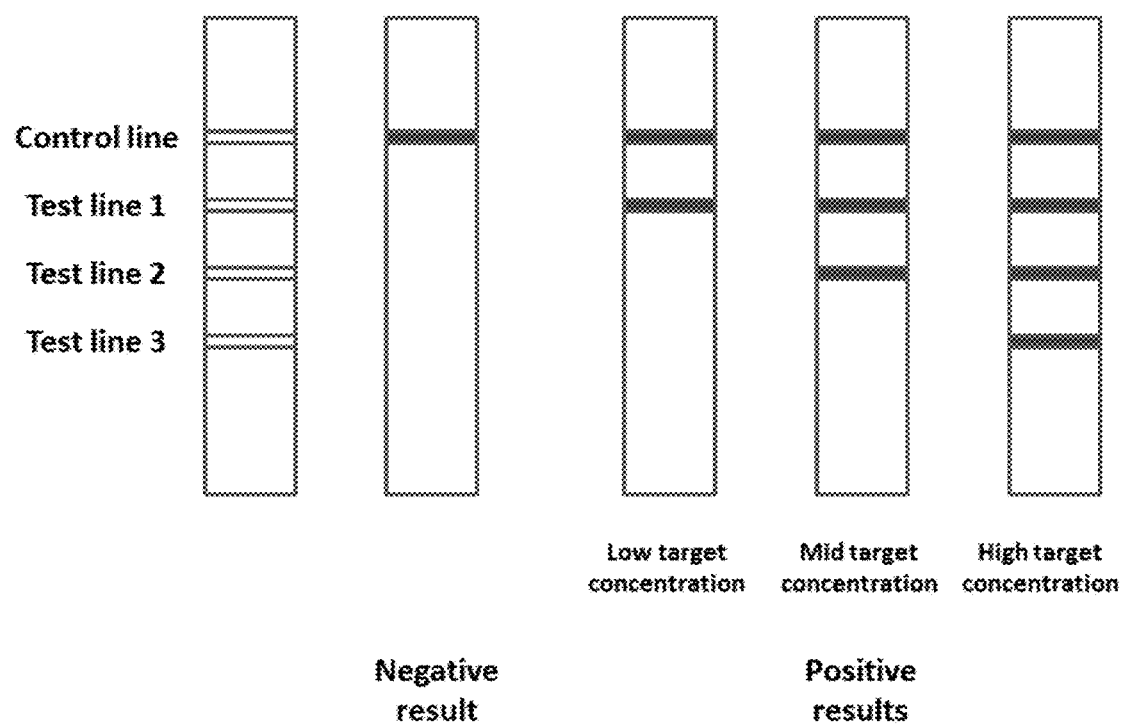
FIG. 3 shows a schematic of a reaction pad demonstrating the concept of a semi-quantitative lateral-flow assay for the detection of S. mutans. The specific antibody for S. mutans is immobilized on the test lines with various concentrations. The number of test lines that appear correlate with the concentration of S. mutans in the samples, which can be used to predict the risk of dental caries development.

In various embodiments the detection components in the assay systems contemplated herein can be paper-based detection components. In certain embodiments the paper-based detection component (can be in the form of a lateral-flow test strip (see, e.g., FIGS. 3 and 10) or a flow-through device (spot test) (see, e.g. FIG. 4). In various embodiments both form factors may contain, but are not limited to, one or more of the following components:

Sample Pad

In certain embodiments a sample pad, when present, can connect the concentration component to the detection component. It can act as a filter that can remove debris, contaminants, and mucus from the collected fluid. It can also store dried reagents, and when rehydrated, these reagents can (i) adjust the solution for optimal detection conditions (pH, ionic strength, etc); and (ii) break down mucus, glycoproteins, and other viscous materials in the collected specimen that may affect detection. Illustrative materials for the sample pad include, but are not limited to, cellulose, nitrocellulose, fiberglass, cotton, woven or nonwoven paper, etc. Reagents on the pad may include, but are not limited to, surfactants such as Triton X-100, Tween 20, or sodium dodecyl sulfate, etc.; polymers such as polyethylene glycol, poloxamer, polyvinylpyrrolidone (PVP), etc.; buffers such as phosphate-buffered saline, 4-(2-hydroxyethyl)-1-piperazineethanesulfonic acid (HEPES), Tris(hydroxymethyl)aminomethane (Tris), sodium borate, TRICINE, etc.; proteins such as albumin, etc.; enzymes such as protease, etc.; salts such as sodium chloride, sodium phosphate, sodium cholate, potassium phosphate, etc. In various embodiments these reagents can be applied to the sample pad by (i) soaking the paper material in the reagent solution, or (ii) through wicking the membrane via capillary flow. The treated sample pad can be dried by (i) air drying (let sit at room temperature); (ii) baking (place in high temperature using an oven or heating device); (iii) vacuum; or (iv) lyophilization.

Conjugate Pad

In various embodiments a conjugate pad, when present can contain dehydrated colorimetric indicators decorated with binding moieties that bind the target analyte(s). In certain embodiments the binding moieties are specific binding moieties that have high affinity towards the target analyte(s) (e.g., bacterium, fungus, virus, etc.). When the sample solution reaches the conjugate pad, the colorimetric indicators are rehydrated. The binding moieties on the colorimetric indicators can then bind to the target analyte(s) and the resulting complexes can flow to the reaction pad. In certain embodiments the colorimetric indicators can comprise metallic particles such as gold, silver particles, polymeric particles such as latex beads, and polystyrene particles encapsulating visible or fluorescent dyes. Illustrative materials material for the conjugate pad include, but are not limited to, cellulose, nitrocellulose, fiberglass, cotton, woven or nonwoven paper etc. In certain embodiments the colorimetric indicators can be applied and dehydrated onto the pad as described above.

Reaction Pad

In certain embodiments the reaction pad, when present, can comprise immobilized reagents, and when the immobilized reagents react with the sample solution, they may produce signals (e.g., visual signals) to indicate the presence or absence or quantity of the target analyte(s). Illustrative materials for the reaction pad include, but are not limited to cellulose, nitrocellulose, fiberglass, cotton, woven or nonwoven paper etc.

Lateral-Flow Format

In certain embodiments for a lateral-flow test strip, the reagents on the reaction pad will be immobilized in the form of lines perpendicular to the direction of flow to ensure all samples can interact with the immobilized reagents. The concentrations of the reagents can be optimized to control the signal intensities, and thus, control the sensitivity of the assay. For example, a semi-quantitative assay can be designed by immobilizing multiple lines of the same reagent with various concentrations. Each line therefore will yield signals only when a specific concentration of target biomolecules is reached. The concentration of the target biomolecules can then be interpreted by counting the number of lines that are visible (see, e.g., FIG. 3). For the detection of S. mutans, this semi-quantitative assay may particularly be useful to provide better prediction of dental caries since S. mutans concentration is highly correlated to the risk of developing dental caries.

In addition, multiple lines of different reagents can be immobilized on the same strip to detect multiple target analyte(s). This allows the development of multiplex assays.

Flow-Through Format

In certain embodiments, e.g., for a flow-through test, instead of lines, the reagents can be immobilized on the entire reaction pad. If the target analyte is present, it will bind to the colorimetric indicator on the conjugate pad and be trapped on the reaction pad as the indicator-target complex binds to the immobilized reagent. A visible spot will therefore appear if the target biomolecule is present. This test can be used if the sample volume is too low to wick up a lateral-flow test strip. The color intensity of the visible spot is correlated to the concentration of target analyte(s) (e.g., biomolecules), while the size of the spot is correlated to the sample volume. In certain embodiments the concentration component can be placed directly on top of the flow-through test to remove the need for extracting and applying the concentrated samples to the detection component (see, e.g., FIG. 4).

In various embodiments the immobilized reagents can comprise a specific antibody against the target analyte (primary antibody), antibodies against the primary antibody (secondary antibody), antigens, proteins, or antigen-protein conjugates. Illustrative materials for the reaction pad include, but are not limited to cellulose, nitrocellulose, fiberglass, cotton, woven and nonwoven paper etc. In various embodiments the reagents can be applied and dehydrated onto the pad as described above.

Sink

In certain embodiments the sink, when present, can comprise an absorbent pad that collect excess fluid and prevents back-flow which can affect the test performance. Illustrative materials for the sink include, but are not limited to cellulose, nitrocellulose, fiberglass, cotton, woven and nonwoven paper etc.

Signal Enhancement

In various embodiments the visible signal intensity can be enhanced to improve the accuracy of the detection assay. This can be performed by introducing additional reagents to the reaction pad after the initial detection assay. In certain embodiments the signal enhancement reagent can comprise a substrate that reacts with an enzyme that is decorated on the surface of, e.g., colorimetric indicator to form a strong visible product. By way of example, if the colorimetric indicator comprises a gold probe, the signal enhancement can be achieved by silver-enhancement labeling, where an enhancement reagent containing silver ion can be applied to the reaction pad where the gold probe is bound to the immobilized line/spot. In this scenario, the gold probes can act as nucleation sites so that silver can be deposited onto the particle, resulting in increased signal intensity. In these examples, the signal enhancement reagents can either be added separately after the initial detection assay, or stored/dehydrated on the paper device to be released automatically/manually.

The foregoing components and assay formats are illustrative and non-limiting. Using the teachings and examples, provided herein, numerous other assay devices and configurations will be available to one of skill in the art and some further design considerations and components are described below.

Lateral-Flow Assay (LFA) or Flow-Through (Spot) Assay

As explained above, in certain embodiments, the devices and systems described herein are configured to provide a lateral-flow assay (LFA) or a flow-through (spot) assay for detection of the target analyte in a sample, where the LFA or spot assay is used alone or in conjunction with an aqueous two-phase system (ATPS). In some embodiments, the LFA or spot assay comprises a porous matrix into which is disposed the ATPS or components thereof, where the porous matrix is configured to and has porosity sufficient to allow the ATPS or components thereof to flow-through the porous matrix when the ATPS or components thereof are in a fluid phase. Such porous LFA or spot assay devices are referred to herein as paper or paper fluidic devices and these terms are used interchangeably.

The term "paper", as used herein, is not limited to thin sheets from the pulp of wood or other fibrous plant substances although, in certain embodiments the use of such papers in the devices described herein is contemplated.

Papers more generally refer to porous materials often in sheet form, but not limited thereto that allow a fluid to flow-through.

In some embodiments, the porous matrix is sufficiently porous to allow the mixed phase solution, first phase solution and/or second phase solution of the ATPS, and/or target analyte, to flow-through the LFA or flow-through assay. In some embodiments, the porous matrix is sufficiently long and/or deep enough for the mixed phase solution, first phase solution and/or second phase solution, and/or target analyte, to flow vertically and/or horizontally through the LFA or flow-through (spot) assay device. In some embodiments, the first phase solution flows through the porous matrix at a first rate and the second phase solution flows through the porous matrix at a second rate, where the first rate and the second rate are different. In some embodiments of the LFA or spot assay the porous matrix comprises inter alia a material such as a sintered glass ceramic, a mineral, cellulose, a fiberglass, a nitrocellulose, polyvinylidene fluoride, a nylon, a charge modified nylon, a polyethersulfone, combinations thereof, and the like.

Concentrate-as-it-Flows

It was discovered that ATPSs can phase separate as the solution flows through a porous substrate (e.g., a paper) which we have termed "concentrate-as-it-flows". Moreover, it was also discovered that flow through the paper significantly speeds up the concentration process. Based this phenomenon, the lateral-flow assay devices and the flow-through assay devices described herein can comprise a paper fluidic component that fully integrates the necessary components for a combined ATPS concentration with the LFA or flow-through detection. It was discovered that when a mixed ATPS solution is applied to certain paper materials, phase separation and analyte concentration occur as the solution flows. We also demonstrated that this phenomenon is preserved even when making an ATPS that had varying volume ratios, e.g., volume of the top phase divided by that of the bottom phase.

Figure 4:
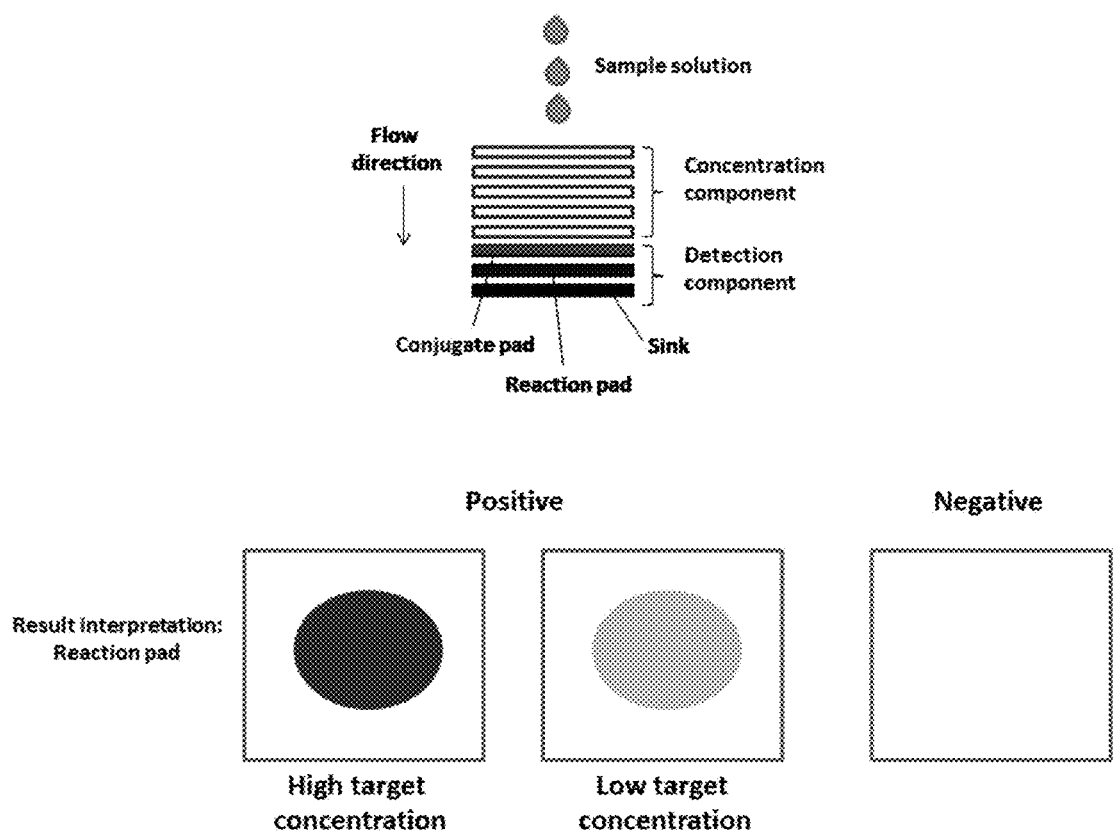
FIG. 4 shows a schematic of an all-in-one spot test for the detection of target biomolecules. ATPS components and colorimetric indicator are dehydrated onto the concentration component and the conjugate pad, respectively. The user can simply apply the sample solution to the device. After which, concentration of the target biomolecules would occur within the concentration component. Subsequently, the solution will rehydrate and bind to the colorimetric indicator on the conjugate pad, and the resulting indicator-target complexes will be captured on the reaction pad as shown by a visible spot.

In some embodiments, the LFA or the spot assay (e.g., the concentration component of the spot assay) comprises a paper. In some embodiments, the paper comprises a sheet of porous material that allows fluid to flow-through it. In some embodiments, the paper comprises a plurality of sheets of porous material that allows fluid to flow-through them (e.g., as illustrated in FIG. 4). In some embodiments, the paper comprises one or more materials such as cellulose, fiberglass, nitrocellulose, polyvinylidine fluoride, charge modified nylon, polyether sulfone, and the like. In some embodiments, the paper is a HI-FLOW PLUS® membrane.

In some embodiments, the paper is a woven paper. In some embodiments, the paper is a Whatman paper. In some embodiments, the Whatman paper comprises Whatman 517, Whatman MF1, Whatman VF1, Whatman Fusion 5, Whatman GF/DVA, Whatman LF1, Whatman CF1, and/or Whatman CF4.

In some embodiments, the paper concentrates the target analyte as the target analyte flows through the LFA or through the concentration component of a flow-through assay (e.g. a "concentrate-as-it-flows"-based device). In some embodiments, the paper concentrates the target analyte as the target analyte flows through the LFA horizontally. In some embodiments, the paper concentrates the target analyte as the target analyte flows through the LFA or flow-through assay vertically.

In some embodiments, the paper has a property that influences which phase solution will become the "leading fluid." By way of non-limiting example, when using a PEG-salt ATPS, adding the solution to fiberglass paper will cause the salt phase to become the leading solution, while using cellulose paper will cause the PEG phase to become the leading solution. In some embodiments, phase separation within the paper accelerates phase separation. Also by way of non-limiting example, a micelle ATPS typically takes several hours to phase separate in a stagnant ATPS, but if applied to a paper strip, this phase separation occurs in minutes. This speeds up the diagnostic process by allowing the ATPSs, which are traditionally the rate-determining step in the process, to become more viable options for our rapid paper diagnostic assays. In some embodiments, the 'concentrate-as-it-flows' device comprises a PEG-salt ATPS (e.g., as illustrated in the Examples). In some embodiments, the 'concentrate-as-it-flows' device comprises a micellar ATPS. In some embodiments, the LFA device or the flow-through assay device comprises fiberglass paper or nitrocellulose paper.

Figure 10:
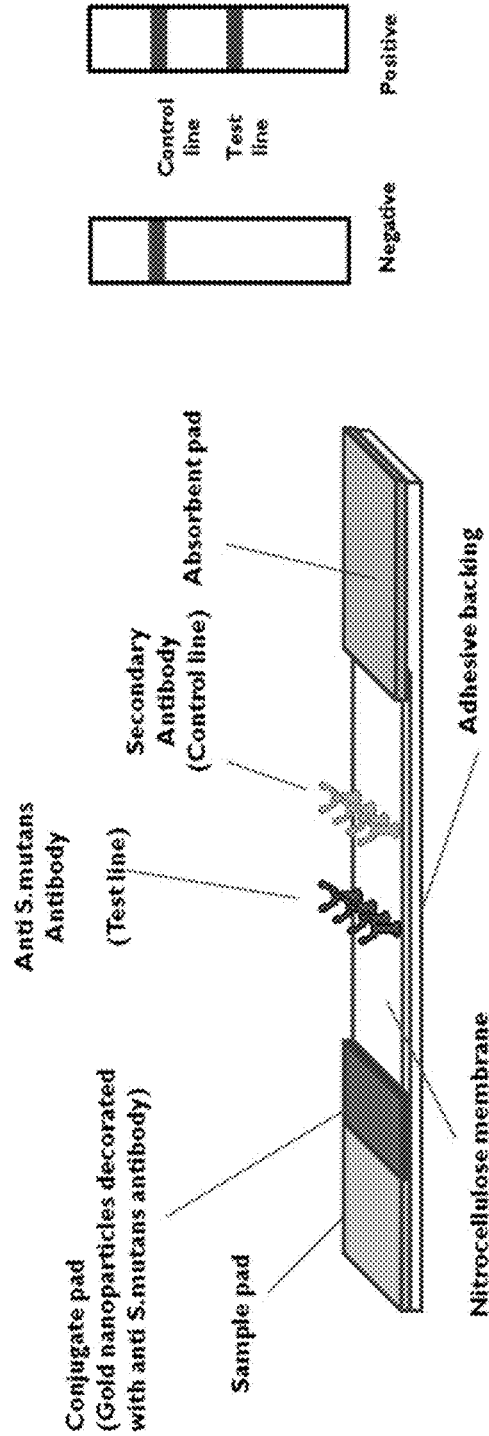
FIG. 10 illustrates one embodiment of a lateral-flow assay (LFA) described herein using a sandwich format.

In certain embodiments the LFA or flow-through assay device comprises a filter that removes debris (e.g., blood cells or other particulates), a sample pad where the sample comprising the target analyte is applied to the device, a detection zone (e.g. test line and control line) where there the target analyte binds and is detected, and an absorbent pad (e.g., a dry receiving paper) that can absorb excess sample and/or solutions applied to the LFA or flow-through device (see, e.g., FIG. 10). In some embodiments, the control line and/or test line is not a line per se, but a region or spot.

In some embodiments, the LFA comprises an LFA strip. The terms "LFA" and "LFA strip" are used interchangeably herein. In some embodiments, the LFA strip has a length greater than its width and depth. In some embodiments, the LFA is rectangular. In some embodiments, the LFA has a shape that is round, ovoid, square, polygonal, or irregular-shaped. In some embodiments, the LFA comprises a plurality of routes and/or junctions. In some embodiments, the LFA strip comprises the sample pad, detection zone and absorbent pad. In some embodiments, the detection zone is located between the sample pad and the absorbent pad, the absorbent pad wicking the sample with the target analyte away from the sample pad and toward the detection zone.

Sandwich Assay

In some embodiments, the LFA or flow-through (spot) assay device is configured to provide or run a sandwich assay (see e.g., FIG. 1, bottom left, in copending PCT Application No: PCT/US2015/019297, filed on Mar. 6, 2015, which is hereby incorporated by reference for the LFA configurations described therein). In some embodiments, the sandwich assay comprises a capture moiety that binds the target analyte. In some embodiments, the device comprises a probe. In some embodiments, the probe comprises a detectable property (colorimetric, fluorescent, radioactive, etc.). In some embodiments, the probe comprises a binding moiety that interacts with the target analyte (e.g. an antibody). In some embodiments, the probe is added to the sample and binds the target analyte to form a probe-analyte complex.

Competition Assay

In some embodiments, the LFA comprises a competition assay. In some embodiments, the probe is added to the sample and binds the target analyte to form a probe-analyte complex. In some embodiments, the LFA comprises the target analyte immobilized on the test line. In some embodiments, the probe is saturated by the target analyte in the sample and the probe will not bind to the target analyte immobilized on the test line. In some embodiments, the absence of the detectable signal on the test line indicates a positive result. In some embodiments, there is no target analyte present in the sample, and the probe binds to the target analyte on the test line, indicating a negative result. In some embodiments, the LFA comprises a probe capture moiety on a control line that interacts directly with the probe, and regardless of the presence of the target analyte in the sample, the probe can bind to the probe capture moiety and accumulate on the control line. In some embodiments, the probe becomes immobilized and detected on the control line, indicating a valid test. In some embodiments, a positive result (e.g., target analyte is present in sample) is indicated by the absence of a detectable signal at the test line and the presence of a detectable signal at the control line. In some embodiments, a negative result is indicated by a detectable signal at both the test and control lines.

In some embodiments of a sandwich format assay, the probe-analyte complex is applied to the sample pad and flows through the LFA or through the flow-through device towards the absorbent pad. In some embodiments, the target analyte of the probe-analyte complex binds to the capture moiety. In some embodiments, the capture moiety is immobilized on a test line or a test region (e.g., a test layer in a flow-through device) and the probe-analyte complex becomes immobilized on the test line or in the test region. In some embodiments, the probe is colorimetric, and the test line or test region will exhibit a strong color (e.g. detectable signal) as the probe-analyte complex accumulates at the test line or in the test region, indicating a positive result. In some embodiments, there is no target analyte present in the sample, and the probe of the probe-analyte complex does not interact with the capture moiety, and the absence of the test line or signal in the test region indicates a negative result. In some embodiments, the LFA comprises a probe capture moiety on a control line (or in a control region, e.g., of a flow-through assay device) that interacts directly with the probe and/or the binding moiety, and thus, regardless of the presence of the target analyte in the sample, the probe/binding moiety binds to the probe capture moiety and accumulate on the control line or in the control region. In some embodiments, the probe capture moiety is a secondary antibody that binds the binding moiety, wherein the binding moiety is a primary antibody that binds that target analyte. In some embodiments, the probe becomes immobilized and detected on the control line or in the control region, indicating a valid test. In some embodiments, a positive result (e.g. target analyte is present in sample) is indicated by a detectable signal at the test line (or test region) and the control line (or control region). In some embodiments, a negative result is indicated by a detectable signal at the control line or in the control region.

Aqueous Two-Phase System (ATPS)

In certain embodiments the devices described herein are configured to work in conjunction with an aqueous two-phase system (ATPS), e.g., in a syringe or other vessel, or they are configured to support an aqueous two-phase system (ATPS). In some embodiments, the ATPS comprises a phase solution. The term "phase solution" generally refers to a first phase solution or a second phase solution of the ATPS. In some embodiments, the phase solution is in a mixed solution (e.g. with the first/second phase solution). In some embodiments, the phase solution is the first/second phase solution after it separates from the mixed solution of the ATPS. In some embodiments, the phase solution is the first/second phase solution after it separates from the mixed solution in the LFA or flow-through assay. In certain embodiments the phase solution can refer to the second phase solution while it is in a mixed state (e.g. with the first phase solution). In some embodiments, the phase solution is a leading fluid in the LFA or flow-through assay. In some embodiments, the phase solution is a lagging fluid in the LFA or flow-through assay.

In some embodiments, the ATPS comprises two aqueous solutions, a first phase solution and a second phase solution that are initially mixed (e.g., a mixed phase solution). In some embodiments, the mixed phase solution is a homogeneous solution, while in certain other embodiments the first phase solution and the second phase solution are immiscible. In some embodiments, the first phase solution and the second phase solution are immiscible, but domains of the first phase solution are mixed with domains of the second phase solution. In some embodiments, the immiscibility is driven by changes in temperature, and/or changes in the concentrations of the different components, such as salt. In some embodiments, the first/second phase solutions comprise components, such as, micelles, salts, and/or polymers.

In some embodiments, the target analyte (e.g., biomolecule, bacterium (or fragment thereof), fungus (or fragment thereof), or virus, and the like) in contact with the ATPS, distributes, partitions, and/or concentrates preferentially into the first phase solution over the second phase solution, or vice versa, based on its physical and chemical properties, such as size, shape, hydrophobicity, and charge. In some embodiments, the target analyte (e.g. a bacterium, fungus, virus, etc.) partitions predominantly (or extremely) into the first or second phase solution of the ATPS, and therefore concentrates in the ATPS. In some embodiments, the target analyte is concentrated by adjusting the ratio of volumes between the first phase solution and the second phase solution. In some embodiments, the target analyte is concentrated by reducing the volume of the phase in which the analyte partitions. By way of illustration, in some embodiments, the target analyte is concentrated by 10-fold in the first phase solution, e.g., by using a 1:9 volume ratio of first phase solution to second phase solution, since the volume of the phase into which the analyte extremely partitions into is ¹⁄₁₀ the total volume.

In some embodiments, other concentrations are obtained by using other ratios. Thus, in some embodiments the ratio of the first phase solution to the second phase solution comprises a ratio of about 1:1, about 1:2, about 1:3, about 1:4, about 1:5, about 1:6, about 1:7, about 1:8, about 1:9, or about 1:10. In some embodiments the ratio of the first phase solution to the second phase solution comprises a ratio of about 1:20, about 1:30, about 1:40, about 1:50, about 1:60, about 1:70, about 1:80, about 1:90, or about 1:100. In some embodiments the ratio of the first phase solution to the second phase solution comprises a ratio of about 1:200, about 1:300, about 1:400, about 1:500, about 1:600, about 1:700, about 1:800, about 1:900, or about 1:1000.

In some embodiments the ratio of the second phase solution to the first phase solution comprises a ratio of about 1:1, about 1:2, about 1:3, about 1:4, about 1:5, about 1:6, about 1:7, about 1:8, about 1:9, or about 1:10. In some embodiments the ratio of the second phase solution to the first phase solution comprises a ratio of about 1:20, about 1:30, about 1:40, about 1:50, about 1:60, about 1:70, about 1:80, about 1:90, or about 1:100. In some embodiments the ratio of the second phase solution to the first phase solution comprises a ratio of about 1:200, about 1:300, about 1:400, about 1:500, about 1:600, about 1:700, about 1:800, about 1:900, or about 1:1000.

In some embodiments, the analyte partitions substantially evenly between the first phase solution and second phase solution, preventing concentration of the analyte. In such systems, concentration of the target analyte can be achieved by introducing an additional component, such as a probe that captures the target analyte, and wherein the probe partitions predominantly into one phase, thereby enhancing the partitioning behavior of the target analyte to enable concentration. In some embodiments, the first/second phase solution containing the concentrated analyte is collected and applied to the LFA or to the flow-through assay device.

In some embodiments, the first/second phase solution comprises a micellar solution. In some embodiments, the micellar solution comprises a nonionic surfactant. In some embodiments, the micellar solution comprises a detergent. In some embodiments, the micellar solution comprises Triton-X. In some embodiments, the micellar solution comprises a polymer similar to Triton-X, such as Igepal CA-630 and Nonidet P-40, and the like, by way of non-limiting example. In some embodiments, the micellar solution consists essentially of Triton-X.

In some embodiments, the micellar solution has a viscosity (at room temperature (~25° C.) of about 0.01 centipoise to about 5000 centipoise, about 0.01 centipoise to about 4500 centipoise, about 0.01 centipoise to about 4000 centipoise, about 0.01 centipoise to about 3500 centipoise, about 0.01 centipoise to about 3000 centipoise, about 0.01 centipoise to about 2500 centipoise, about 0.01 centipoise to about 2000 centipoise, about 0.01 centipoise to about 1500 centipoise, about 0.01 centipoise to about 1000 centipoise, or about 0.01 centipoise to about 500 centipoise. In some embodiments, the micellar solution has a viscosity at room temperature of about 0.01 centipoise to about 450 centipoise, about 0.01 centipoise to about 400 centipoise, about 0.01 centipoise to about 350 centipoise, about 0.01 centipoise to about 300 centipoise, about 0.01 centipoise to about 250 centipoise, about 0.01 centipoise to about 200 centipoise, about 0.01 centipoise to about 150 centipoise, or about 0.01 centipoise to about 100 centipoise.

In some embodiments, the first/second phase solution comprises a polymer (e.g., polymer solution). In certain embodiments, the polymer is a polyethylene glycol (PEG). In various embodiments, the PEG may have a molecular weight between 1000 and 100,000. In certain embodiments, the PEG comprises PEG-4600, PEG-8000, or PEG-20,000. In certain embodiments, the polymer is polypropylene glycol (PPG). In various embodiments, the PPG may have a molecular weight between 100 and 10,000. In certain embodiments, the PPG comprises PPG 425. In certain embodiments, the polymer is dextran. In various embodiments, the dextran may have a molecular weight between 1000 and 1,000,000. In certain embodiments, the dextran comprises dextran 6000, dextran 9000, dextran-35,000, or dextran-200,000.

In some embodiments, the polymer solution comprises a polymer solution that is about 0.01% w/w polymer, or about 0.05% w/w polymer, or about 0.1% w/w polymer, or about 0.15% w/w polymer, or about 0.2% w/w polymer, or about 0.25% w/w polymer, or about 0.3% w/w polymer, or about 0.35% w/w polymer, or about 0.4% w/w polymer, or about 0.45% w/w polymer, or about 0.5% w/w polymer, or about 0.55% w/w polymer, or about 0.6% w/w polymer, or about 0.65% w/w polymer, or about 0.7% w/w polymer, or about 0.75% w/w polymer, or about 0.8% w/w polymer, or about 0.85% w/w polymer, or about 0.9% w/w polymer, or about 0.95% w/w polymer, or about 1% w/w polymer. In some embodiments, the polymer solution comprises a polymer solution that is about 1% w/w polymer, or about 2% w/w polymer, or about 3% w/w polymer, or about 4% w/w polymer, or about 5% w/w polymer, or about 6% w/w polymer, or about 7% w/w polymer, or about 8% w/w polymer, or about 9% w/w polymer, or about 10% w/w polymer, or about 110% w/w polymer, or about 12% w/w polymer, or about 13% w/w polymer, or about 14% w/w polymer, or about 15% w/w polymer, or about 16% w/w polymer, or about 17% w/w polymer, or about 18% w/w polymer, or about 19% w/w polymer, or about 20% w/w polymer, or about 21% w/w polymer, or about 22% w/w polymer, or about 23% w/w polymer, or about 24% w/w polymer, or about 25% w/w polymer, or about 26% w/w polymer, or about 27% w/w polymer, or about 28% w/w polymer, or about 29% w/w polymer, or about 30% w/w polymer, or about 31% w/w polymer, or about 32% w/w polymer, or about 33% w/w polymer, or about 34% w/w polymer, or about 35% w/w polymer, or about 36% w/w polymer, or about 37% w/w polymer, or about 38% w/w polymer, or about 39% w/w polymer, or about 40% w/w polymer, or about 41% w/w polymer, or about 42% w/w polymer, or about 43% w/w polymer, or about 44% w/w polymer, or about 45% w/w polymer, or about 46% w/w polymer, or about 47% w/w polymer, or about 48% w/w polymer, or about 49% w/w polymer, or and about 50% w/w polymer. In some embodiments, the polymer solution comprises a polymer solution that is about 10% w/w polymer, or about 20% w/w polymer, or about 30% w/w polymer, or about 40% w/w polymer, or about 50% w/w polymer, or about 60% w/w polymer, or about 70% w/w polymer, or about 80% w/w polymer, or about 90% w/w polymer. In some embodiments, the polymer solution comprises a polymer solution that is about 10% w/w polymer to about 80% w/w polymer. In some embodiments, the polymer solution comprises a polymer solution that is about 10% w/w to about 25% w/w polymer.

In some embodiments, the first and/or second phase solution comprises a salt and thereby forms a salt solution. In some embodiments, the target analyte (e.g., bacterium, fungus, virus, etc.) and/or a probe-analyte complex partitions into the salt solution. In certain embodiments the salt solution comprises a kosmotropic salt. In some embodiments the salt solution comprises a chaotropic salt. In some embodiments, the salt comprises one or more of a magnesium salt, a lithium salt, a sodium salt, a potassium salt, a cesium salt, a zinc salt, and an aluminum salt. In some embodiments, the salt comprises a bromide salt, an iodide salt, a fluoride salt, a carbonate salt, a sulfate salt, a citrate salt, a carboxylate salt, a borate salt, or a phosphate salt. In some embodiments, the salt is potassium phosphate. In some embodiments, the salt is ammonium sulfate.

In some embodiments, the salt solution comprises a salt solution comprising about 0.01% w/w salt, or about 0.05% w/w salt, about 0.1% w/w salt, or about 0.15% w/w salt, or about 0.2% w/w salt, or about 0.25% w/w salt, or about 0.3% w/w salt, or about 0.35% w/w salt, or about 0.4% w/w salt, or about 0.45% w/w salt, or about 0.5% w/w salt, or about 0.55% w/w salt, or about 0.6% w/w salt, or about 0.65% w/w salt, or about 0.7% w/w salt, or about 0.75% w/w salt, or about 0.8% w/w salt, or about 0.85% w/w salt, or about 0.9% w/w salt, or about 0.95% w/w salt, or about or about 1% w/w salt. In some embodiments, the salt solution comprises a salt solution that is about 1% w/w salt, or about 2% w/w salt, or about 3% w/w salt, or about 4% w/w salt, or about 5% w/w salt, or about 6% w/w salt, or about 7% w/w salt, or about 8% w/w salt, or about 9% w/w salt, or about 10% w/w salt, or about 11% w/w salt, or about 12% w/w salt, or about 13% w/w salt, or about 14% w/w salt, or about 15% w/w salt, or about 16% w/w salt, or about 17% w/w salt, or about 18% w/w salt, or about 19% w/w salt, or about 20% w/w salt, or about 21% w/w salt, or about 22% w/w salt, or about 23% w/w salt, or about 24% w/w salt, or about 25% w/w salt, or about 26% w/w salt, or about 27% w/w salt, or about 28% w/w salt, or about 29% w/w salt, or about 30% w/w salt, or about 31% w/w salt, or about 32% w/w salt, or about 33% w/w salt, or about 34% w/w salt, or about 35% w/w salt, or about 36% w/w salt, or about 37% w/w salt, or about 38% w/w salt, or about 39% w/w salt, or about 40% w/w salt, or about 41% w/w salt, or about 42% w/w salt, or about 43% w/w salt, or about 44% w/w salt, or about 45% w/w salt, or about 46% w/w salt, or about 47% w/w salt, or about 48% w/w salt, or about 49% w/w salt, or and about 50% w/w. In some embodiments, the salt solution comprises a salt solution that is about 0.1% w/w to about 10%. In some embodiments, the salt solution is about 1% w/w to about 10%.

In some embodiments, the first/second phase solution comprises a solvent that is immiscible with water. In some embodiments, the solvent comprises anon-polar organic solvent. In some embodiments, the solvent comprises an oil. In some embodiments, the solvent comprises pentane, cyclopentane, benzene, 1,4-dioxane, diethyl ether, dichloromethane, chloroform, toluene, or hexane.

In some embodiments, the first phase solution comprises a micellar solution and the second phase solution comprises a polymer. In some embodiments, the second phase solution comprises a micellar solution and the first phase solution comprises a polymer. In some embodiments, the first phase solution comprises a micellar solution and the second phase solution comprises a salt. In some embodiments, the second phase solution comprises a micellar solution and the first phase solution comprises a salt. In some embodiments, the micellar solution is a Triton-X solution. In some embodiments, the first phase solution comprises a first polymer and the second phase solution comprises a second polymer. In some embodiments, the first/second polymer comprises polyethylene glycol and/or dextran. In some embodiments, the first phase solution comprises a polymer and the second phase solution comprises a salt. In some embodiments, the second phase solution comprises a polymer and the first phase solution comprises a salt. In some embodiments, the first phase solution comprises polyethylene glycol and the second phase solution comprises potassium phosphate. In some embodiments, the second phase solution comprises polyethylene glycol and the first phase solution comprises potassium phosphate. In some embodiments, the first phase solution comprises a salt and the second phase solution comprises a salt. In some embodiments, the first phase solution comprises a kosmotropic salt and the second phase solution comprises a chaotropic salt. In some embodiments, the second phase solution comprises a kosmotropic salt and the first phase solution comprises a chaotropic salt.

In some embodiments, the first phase solution comprises a Component 1 of Table 1 and the second phase solution comprises a Component 2 of Table 1. In some embodiments, the second phase solution comprises a Component 1 of Table 1 and the second phase solution comprises a Component 2 of Table 1.

In some embodiments, the components of Table 1 are suspended or dissolved in a buffer. In some embodiments, the components of Table 1 are suspended/dissolved in a buffer compatible with a biological system from which the sample was derived. In some embodiments, the components of Table 1 are suspended/dissolved in a saline solution. In some embodiments, the components of Table 1 are suspended/dissolved in PBS. In some embodiments, the components of Table 1 are suspended/dissolved in water.

TABLE 1

Illustrative aqueous two-phase extraction/concentration systems.

| Component 1 | Component 2 |
|---|---|
| Polymer/polymer Systems | |
| Polyethylene glycol | Dextran |
| | Ficoll |
| | Polyvinyl pyrrolidone |
| | Polyvinyl alcohol |
| | Hydroxypropyl starch |
| Polypropylene glycol | Dextran |
| | Hydroxypropyl dextran |
| | Polyvinyl pyrrolidone |
| Polyvinyl alcohol | Dextran |
| | Hydroxypropyl dextran |
| Polyvinyl pyrrolidone | Dextran |
| | Maltodextrin |
| Methyl cellulose | Dextran |
| | Hydroxypropyl dextran |
| Ethylhydroxyethyl cellulose | Dextran |
| Polymer/salt Systems | |
| Polyethylene glycol | Potassium phosphate |
| | Sodium sulfate |
| | Magnesium sulfate |
| | Ammonium sulfate |
| | Sodium citrate |
| Propylene glycol (PPG) | Potassium phosphate |
| Methoxypolyethylene glycol | Potassium phosphate |
| Polyvinyl pyrrolidone | Potassium phosphate |

As illustrated in the Examples, in certain embodiments the ATPS comprises a polymer/salt ATPS. It was discovered that an ATPS comprising polyethylene glycol and a salt or polypropylene glycol and a salt provides a rapid, sensitive, and accurate analyte detection/quantification.

In some embodiments, the devices described herein (e.g., an LFA or a flow-through assay device) can further comprise a collector configured to be placed in contact with the ATPS, wherein the target analyte partitions at an interface of the collector and the first phase solution and/or second phase solution. In some embodiments, the collector comprises a material that is a plastic, a mesoporous material, a silica, a polypropylene, a magnet, a magnetic particle, a paramagnetic particle, a material with a pore, a material with a groove, and/or any combination thereof. In some embodiments, the collector comprises polypropylene. In some embodiments, collector is optimized to increase target analyte collection. In some embodiments, the collector comprises a pore to maximize the surface area. In some embodiments, the width of the pore is about 1 µm, about 5 µm, about 10 µm, about 15 µm, about 20 µm, about 25 µm, about 30 µm, about 35 µm, about 40 µm, about 45 µm, about 50 µm, about 55 µm, about 60 µm, about 65 µm, about 70 µm, about 75 µm, about 80 µm, about 85 µm, about 90 µm, about 95 µm, or about 100 µm. In some embodiments, the width of the pore is about 100 µm, about 200 µm, about 300 µm, about 400 µm, about 500 µm, about 600 µm, about 700 µm, about 800 µm, about 900 µm, or about 1 mm. In some embodiments, the depth of the pore is about 1 µm, about 5 µm, about 10 µm, about 15 µm, about 20 µm, about 25 µm, about 30 µm, about 35 µm, about 40 µm, about 45 µm, about 50 µm, about 55 µm, about 60 µm, about 65 µm, about 70 µm, about 75 µm, about 80 µm, about 85 µm, about 90 µm, about 95 µm, or about 100 µm. In some embodiments, the depth of the pore is about 100 µm, about 200 µm, about 300 µm, about 400 µm, about 500 µm, about 600 µm, about 700 µm, about 800 µm, about 900 µm, or about 1 mm.

Dehydrated ATPS in LFA or Flow-Through (Spot) Assay Device.

In some embodiments, the ATPS or components thereof are dehydrated on and/or in at least a first portion of the porous matrix comprising an LFA or in the concentration component of a flow-through assay device. In some embodiments, application of the sample to the device hydrates the ATPS, thereby converting the ATPS or components thereof to a fluid phase. Dehydration may make the device more user friendly as the user just needs to add the sample (e.g., saliva, blood, urine, vaginal fluid, seminal fluid, sputum, cerebrospinal fluid, lymph, or similar fluid) to the device. In some embodiments, a user only has to apply a solution of the sample to the strip to detect the presence/absence of the target analyte or to quantify the analyte. In some embodiments, the solution of the sample flows through the LFA or the flow-through device and the ATPS is re-solubilized, triggering phase separation within the LFA or flow-through device and subsequent concentration of the target analyte.

In some embodiments, all the necessary components for a given ATPS are mixed to form a mixed solution, applied to the paper comprising the device (e.g., LFA or flow-through (spot) assay), and then dehydrated. When the sample solution is added to the dehydrated paper, the ATPS components are rehydrated as the sample flows, resulting in phase separation. In some ATPSs where the phase containing the concentrated analyte is less viscous, that phase will flow faster and the concentrated analyte will emerge in the leading fluid and will reach the detection zone of the LFA or flow-through assay to initiate detection. Additionally, the dehydrated ATPS component segment length (or thickness) and concentration can be adjusted for different applications.

In some embodiments, both (all) components of the ATPS are dehydrated on the LFA or in the flow-through assay (e.g., in the separation component). In some embodiments, a first ATPS component is dehydrated on (or in) the LFA or in the flow-through assay. In some embodiments, a second ATPS component is dehydrated on or in the LFA or flow-through assay. In some embodiments, the first phase solution component and/or first ATPS component is dehydrated on a first portion of the LFA or in a first layer of the flow-through assay (separation component). In some embodiments, the second phase solution component and/or second ATPS component is dehydrated on a second portion of the LFA or in a second layer of the flow-through assay (separation component). In some embodiments, the first portion and the second portion are same. In some embodiments, the first portion and the second portion are different. By way of non-limiting example, in a PEG-salt ATPS, the PEG and salt solutions can be dehydrated separately into different paper portions or segments (see, e.g., FIG. 16 of copending PCT Application No: PCT/US2015/019297, filed on Mar. 6, 2015, which is hereby incorporated by reference for the LFA configurations described therein) or in separate layers comprising, e.g., the separation component of a flow-through assay (see, e.g., FIG. 4). In some embodiments, dehydrating the first/second phase solution and/or ATPS component on different portions of the LFA or in different layers of the flow-through assay provides a more uniform concentration of the first/second phase solution components or ATPS components. In some embodiments, dehydrating the first/second phase solution components and/or ATPS components on different portions allows the first phase solution or ATPS component to flow in a first direction after hydration and the second phase solution and/or ATPS component to flow in a second direction after hydration, wherein the first and second directions are different. In some embodiments, the target analyte is concentrated in the first direction, but not the second direction. In some embodiments, the target analyte is concentrated in the second direction, but not the first direction. In some embodiments, dehydrating the first/second phase components and/or ATPS components on different portions allows the target analyte to flow in the first/second direction without requiring the sample to flow in the first/second direction. In some embodiments, dehydrating the first/second phase components and/or ATPS components on different portions allows the target analyte to flow faster, resulting in detection sooner. In some embodiments, dehydrating the first/second phase components and/or ATPS components on different portions allows for increased result reliability. In some embodiments, dehydrating the first/second phase components and/or ATPS components on different portions prevents aggregation of first/second phase solution components and/or ATPS components (e.g. PEG-salt ATPS). In some embodiments, the first/second phase component and/or ATPS component is dehydrated in multiple segments. In some embodiments the first/second phase component and/or ATPS component is dehydrated in multiple segments, wherein the first/second phase component and/or ATPS component comprises a salt solution. In some embodiments the first/second phase component and/or ATPS component is dehydrated in multiple segments, wherein the first/second phase component and/or ATPS component does not comprise a polymer (e.g. PEG). In some embodiments, dehydrated PEG is not located near the detection zone because the PEG-rich phase can slow the flow within the detection membrane. In some embodiments, the LFA strip or the flow-through assay can comprise a blank spacer near the detection zone that does not contain PEG or salt.

In some embodiments, a probe (e.g., an analyte binding moiety and associated detection reagent/material) is provided in a probe buffer. In some embodiments, the probe buffer is dehydrated on the LFA or in the flow-through assay.

In some embodiments, dehydration of ATPS components improves the limit of detection compared to a device in which the ATPS components are added in liquid form. In some embodiments, the addition of liquid form ATPS components dilutes the sample solution from the subject. In some embodiments, dehydration of ATPS components allows for a distinct first phase solution and/or distinct second phase solution to develop during flow, concentrating the target analyte or probe-analyte complex in a small volume at the front of the leading fluid that will reach the test and control lines or the detection component of a flow-through assay. In some embodiments, concentrating the target analyte and or probe-analyte complex at the front of the leading fluid will decrease the time period necessary for detection.

Probes

In certain embodiments the systems and/or devices described herein and/or the methods described herein utilize a probe, where the probe comprises a binding moiety that binds the target analyte to form a probe-analyte complex.

In some embodiments, the target analyte alone partitions preferentially into the first phase solution or second phase solution or interface of the first phase solution and second phase solution. In some embodiments, the target analyte alone partitions extremely into the first phase solution or second phase solution or interface of the first phase solution and second phase solution.

In some embodiments, the target analyte alone does not partition preferentially into the first phase solution or second phase solution or interface of the first phase solution and second phase solution. In some embodiments, the target analyte alone does not partition extremely into the first phase solution or second phase solution or interface of the first phase solution and second phase solution.

In some embodiments, the probe-analyte complex partitions preferentially into the first phase solution or second phase solution or interface of the first phase solution and second phase solution, thereby causing the target analyte (of the probe-analyte complex) to partition preferentially into the first phase solution or second phase solution or interface of the first phase solution and second phase solution.

In some embodiments, the probe-analyte complex partitions extremely into the first phase solution or second phase solution or interface of the first phase solution and second phase solution, thereby causing the target analyte (of the probe-analyte complex) to partition extremely into the first phase solution or second phase solution or interface of the first phase solution and second phase solution.

In some embodiments, the phrase "partitions preferentially," when used with respect to the partitioning of the target analyte (or probe-analyte complex) to a first/second phase solution of the ATPS, indicates that a greater amount of the target analyte becomes disposed in a preferred phase solution than in another phase solution of the ATPS.

In some embodiments, the phrase "partitions extremely," when used with respect to the partitioning of the target analyte (or probe-analyte complex) to a first/second phase solution of the ATPS, indicates that about 90% or more of the target analyte becomes disposed in a preferred phase solution than in another phase solution of the ATPS.

In some embodiments, a greater amount of the target analyte partitions into the first phase solution. In some embodiments, greater than about 50%, or greater than about 55%, or greater than about 60%, or greater than about 65%, or greater than about 70%, or greater than about 75%, or greater than about 80%, or greater than about 85%, or greater than about 90%, or greater than about 95%, or greater than about 98%, or greater than about 99% of the target analyte partitions into the first phase solution. In some embodiments, greater than about 99%, or greater than about 99.1%, or greater than about 99.2%, or greater than about 99.3%, or greater than about 99.4%, or greater than about 99.5%, or greater than about 99.6%, or greater than about 99.7%, or greater than about 99.8%, or greater than about 99.9% of the target analyte partitions into the first phase solution.

In some embodiments, a greater amount of the analyte partitions into the second phase solution. In some embodiments, greater than about 50%, or greater than about 55%, or greater than about 60%, or greater than about 65%, or greater than about 70%, or greater than about 75%, or greater than about 80%, or greater than about 85%, or greater than about 90%, or greater than about 95%, or greater than about 98%, or greater than about 99% of the target analyte partitions into the second phase solution. In some embodiments, greater than about 99%, or greater than about 99.1%, or greater than about 99.2%, or greater than about 99.3%, or greater than about 99.4%, or greater than about 99.5%, or greater than about 99.6%, or greater than about 99.7%, or greater than about 99.8%, or greater than about 99.9% of the target analyte partitions into the second phase solution.

In some embodiments, a greater amount of the analyte partitions into the interface of the first phase solution and the second phase solution. In some embodiments, greater than about 50%, or greater than about 55%, or greater than about 60%, or greater than about 65%, or greater than about 70%, or greater than about 75%, or greater than about 80%, or greater than about 85%, or greater than about 90%, or greater than about 95%, or greater than about 98%, or greater than about 99% of the target analyte partitions into the interface. In some embodiments, greater than about 99%, or greater than about 99.1%, or greater than about 99.2%, or greater than about 99.3%, or greater than about 99.4%, or greater than about 99.5%, or greater than about 99.6%, or greater than about 99.7%, or greater than about 99.8%, or greater than about 99.9% of the target analyte partitions into the interface.

In some embodiments, the device comprises or is configured to utilize and/or the assay run on the device utilizes 1 probe. In some embodiments, the device comprises or is configured to utilize and/or the assay run on the device utilizes at least two different probes, or at least 3 different probes, or at least 4 different probes, or at least 5 different probes, or at least 7 different probes, or at least 10 different probes, or at least 15 different probes, or at least 20 different probes.

In some embodiments, the probe comprises one or more of a synthetic polymer, a metal, a mineral, a glass, a quartz, a ceramic, a biological polymer, a plastic, and/or combinations thereof. In some embodiments, the probe comprises a polymer comprises a polyethylene, polypropylene, nylon (DELRIN®), polytetrafluoroethylene (TEFLON®), dextran and polyvinyl chloride. In some embodiments, the polyethylene is polyethylene glycol. In some embodiments, the polypropylene is polypropylene glycol. In some embodiments, the probe comprises a biological polymer that comprises one or more of a collagen, cellulose, and/or chitin. In some embodiments, the probe comprises a metal that comprises one or more of gold, silver, platinum titanium, stainless steel, aluminum, or alloys thereof. In some embodiments, the probe comprises a nanoparticle (e.g., a gold nanoparticle, a silver nanoparticle, etc.).

In some embodiments, the probe further comprises a coating. In some embodiments, the coating comprises polyethylene glycol or polypropylene glycol. In some embodiments, the coating comprises polypropylene. In some embodiments, the coating comprises polypropylene glycol. In some embodiments, the coating comprises dextran. In some embodiments, the coating comprises a hydrophilic protein. In some embodiments, the coating comprises serum albumin. In some embodiments, the coating has an affinity for the first phase solution or the second phase solution.

In some embodiments, the amount of target analyte in the sample is very low, such that the analyte needs to be substantially concentrated to enable detection by LFA or flow-through assay. In certain embodiments, substantial concentration is achieved at an interface, since the degree of analyte concentration is dependent on the volume of a phase in which the analyte partitions, or concentrates, and the "volume" at the interface is very small relative to the bulk phases.

In some embodiments, the probe partitions preferentially (or extremely) to the interface in order to drive the target analyte towards an interface. In some embodiments, the probe partitions preferentially (or extremely) to the interface due to their surface chemistry, wherein the surface chemistry is optimized to drive the probe to the interface. By way of non-limiting example, to drive the probe-analyte complex to the interface of a polymer-salt ATPS system, such as the polyethylene glycol-potassium phosphate (PEG/salt) system, the probes are conjugated to PEG (or PEGylated) to promote the PEG-PEG interaction with the PEG-rich phase, and/or are decorated with hydrophilic proteins to promote hydrophilic interactions with the PEG-poor phase. Using such an optimized probe decorated with specific antibodies or other molecules capable of binding to the target, the target analyte is captured and collected at the interface. Since the volume of the interface is very small, the analytes are highly concentrated and are applied to the subsequent LFA or detection region of the flow-through assay.

In some embodiments, gold nanoprobes (GNP) are prepared that are capable of partitioning to the interface of a PEG/salt ATPS, and operating conditions are optimized to allow for a fast phase separation time with a very high recovery of GNP/analyte.

In some embodiments, the probe-analyte complex partitions to a solid-liquid interface in the ATPS. In some embodiments, the solid is the wall of the chamber that contains the ATPS. In some embodiments, the solid is the collector of the assay device. In some embodiments, the solid comprises a solid polymer. In some embodiments, the solid polymer comprises polyethylene, cellulose, chitin, nylon, polyoxymethylene (DELRIN®), polytetrafluoroethylene (TEFLON®), polyvinyl chloride, or combinations thereof. In some embodiments, the solid polymer comprises polypropylene. In some embodiments, the probe-analyte complex sticks to the solid and is highly concentrated since it is present in the small volume at the solid-liquid interface, and not diluted by the volume of the bulk phases. In some embodiments, the bulk phase is removed without disrupting the concentrated analyte, and is collected by washing, with subsequent application to the LFA or to the flow-through assay device. In some embodiments, this approach significantly concentrates the analyte and allows collection without using an external force (e.g., magnet). Alternatively, the probe comprises a magnetic material and this approach is used with a magnet. In some embodiments, these probes are modified to be concentrated at the interface for extreme analyte concentration. As mentioned above, this approach can provide additional separation of the target analyte from other contaminants, which is nonspecifically concentrated by ATPS, through the use of a magnet. In some embodiments, the ATPS concentration enables the magnetic probe to work more efficiently, since the magnetic probe would first be concentrated into a very small volume at a specific location (the interface). Accordingly, a smaller magnet or a weaker magnetic field will be required to collect the concentrated analyte. In some embodiments, the combination of ATPS interface concentration with magnetic probes allows for the development of a more effective, rapid, and cheaper device compared to the current state-of-the-art.

Binding Moiety

In some embodiments, the binding moiety is a molecule that binds the target analyte (e.g., bacterium, fungus, virus, etc.). In some embodiments, the binding moiety is a molecule that specifically binds the target analyte. In some embodiments, "specifically binds" indicates that the molecule binds preferentially to the target analyte or binds with greater affinity to the target analyte than to other molecules. By way of non-limiting example, an antibody will selectively bind to an antigen against which it was raised. Also, by way of non-limiting example, a DNA molecule will bind to a substantially complementary sequence and not to unrelated sequences under stringent conditions. In some embodiments, "specific binding" can refer to a binding reaction that is determinative of the presence of a target analyte in a heterogeneous population of molecules (e.g., proteins and other biologics). In some embodiments, the binding moiety binds to its particular target analyte and does not bind in a significant amount to other molecules present in the sample.

In some embodiments, the binding moiety comprises an antibody, a lectin, a protein, a glycoprotein, a nucleic acid, monomeric nucleic acid, a polymeric nucleic acid, an aptamer, an aptazyme, a small molecule, a polymer, a lectin, a carbohydrate, a polysaccharide, a sugar, a lipid, or any combination thereof. In some embodiments, the binding moiety is a molecule capable of forming a binding pair with the target analyte.

In some embodiments, the binding moiety is an antibody or antibody fragment. Antibody fragments include, but are not limited to, Fab, Fab', Fab'-SH, F(ab')$_2$, Fv, Fv', Fd, Fd', scFv, hsFv fragments, cameloid antibodies, diabodies, and other fragments described below.

In some embodiments, an "antibody" refers to a protein consisting of one or more polypeptides substantially encoded by immunoglobulin genes or fragments of an immunoglobulin gene. As used herein, the terms "antibody" and "immunoglobulin" are used interchangeably, unless otherwise specified. In some embodiments, the immunoglobulin gene is an immunoglobulin constant region gene. In some embodiments, the immunoglobulin gene, is by non-limiting example, a kappa, lambda, alpha, gamma, delta, epsilon or mu constant region gene. In some embodiments, the immunoglobulin gene is an immunoglobulin variable region gene. In some embodiments, the immunoglobulin gene comprises a light chain. In some embodiments, the light chain comprises a kappa light chain, a lambda light chain or a combination thereof. In some embodiments, the immunoglobulin gene comprises a heavy chain. In some embodiments, the heavy chain is classified as gamma, mu, alpha, delta, or epsilon, which in turn correspond to the immunoglobulin classes, IgG, IgM, IgA, IgD and IgE, respectively.

In some embodiments, the immunoglobulin comprises a tetramer. In some embodiments, the tetramer is composed of two identical pairs of polypeptide chains, each pair having one "light" (about 25 kDa) and one "heavy" chain (about 50-70 kDa). In some embodiments, the N-terminus of each chain defines a variable region of about 100 to 110 or more amino acids primarily responsible for antigen recognition. The terms variable light chain ($V_L$) and variable heavy chain ($V_H$) refer to these light and heavy chains, respectively.

In some embodiments, the antibody comprises an intact immunoglobulin. In some embodiments, the antibody comprises a number of well characterized fragments produced by digestion with various peptidases. In some embodiments, the peptidase is pepsin. In some embodiments, the pepsin digests a disulfide linkage in the hinge region to produce F(ab)'$_2$, a dimer of Fab which itself is a light chain joined to $V_H$-$C_H$1 by a disulfide bond. In some embodiments, the F(ab)'$_2$ is reduced under mild conditions to break the disulfide linkage in the hinge region thereby converting the (Fab')$_2$ dimer into a Fab' monomer. In some embodiments, the Fab' monomer consists essentially of a Fab with part of the hinge region. In some embodiments, the Fab' fragment is synthesized de novo either chemically or by utilizing recombinant DNA methodology. In some embodiments, the antibody fragment is produced by the modification of a whole antibody. In some embodiments, the antibody fragment is synthesized de novo using recombinant DNA methodologies. In some embodiments, the antibody includes a single chain antibody (antibodies that exist as a single polypeptide chain). In some embodiments, the antibody includes a single chain Fv antibody (sFv or scFv) in which a variable heavy and a variable light chain are joined together (directly or through a peptide linker) to form a continuous polypeptide. In some embodiments, the antibody includes a single chain Fv antibody. In some embodiments, the antibody comprises a covalently linked $V_H$-$V_L$ heterodimer which may be expressed from a nucleic acid including $V_H$- and $V_L$-encoding sequences either joined directly or joined by a peptide-encoding linker. In some embodiments, the $V_H$ and $V_L$ are connected to each as a single polypeptide chain, and the $V_H$ and $V_L$ domains associate non-covalently. In some embodiments, the Fab is displayed on a phage, wherein one of the chains (heavy or light) is fused to g3 capsid protein and the complementary chain exported to the periplasm as a soluble molecule. In some embodiments, the two chains can be encoded on the same or on different replicons. In some embodiments, the two antibody chains in each Fab molecule assemble post-translationally and the dimer is incorporated into the phage particle via linkage of one of the chains to, e.g., g3p. In some embodiments, the antibody has been displayed on a phage or yeast.

In some embodiments, the antibody fragment is derived via proteolytic digestion of intact antibodies. In some embodiments, the antibody fragment is produced directly by recombinant host cells. In some embodiments, the Fab, Fv or scFv antibody fragment is expressed in and secreted from E. coli, thus allowing the facile production of large amounts of these. In some embodiments, the antibody fragment is isolated from antibody phage libraries. In some embodiments, the Fab'-SH fragments can be directly recovered from E. coli and chemically coupled to form $F(ab')_2$ fragments. In some embodiments, the $F(ab')_2$ fragment is isolated directly from recombinant host cell culture. In some embodiments, the Fab and $F(ab')_2$ fragments have an increased in vivo half-life. In some embodiments, the Fab and $F(ab')_2$ fragments comprise salvage receptor binding epitope residues. Other techniques for the production of antibody fragments will be apparent to the skilled practitioner. In certain embodiments, the antibody of choice is a single chain Fv fragment. In some embodiments, the Fv or sFv has an intact combining site that is devoid of a constant region; thus, it is suitable for reduced non-specific binding during in vivo use. In some embodiments, the antibody fragment is a "linear antibody." In some embodiments, the linear antibody fragment is monospecific. In some embodiments, the linear antibody fragment is bispecific.

In some embodiments, the antibody fragment is a diabody. In some embodiments, the diabody is an antibody fragment with two antigen binding sites that may be bivalent or bispecific.

In some embodiments, the antibody fragment is a single-domain antibody. In some embodiments, the single-domain antibody is an antibody fragment comprising all or a portion of the heavy chain variable domain or all or a portion of the light chain variable domain of an antibody. In certain embodiments, a single-domain antibody is a human single-domain antibody.

In certain embodiments, the binding moiety comprises an aptamer. In some embodiments, the aptamer comprises an antibody-analogue formed from nucleic acids. In some embodiments, the aptamer does not require binding of a label to be detected in some assays, such as nano-CHEM-FET, where the reconfiguration would be detected directly. In some embodiments, the binding moiety comprises an aptazyme. In some embodiments, the aptazyme comprises an enzyme analogue, formed from nucleic acids. In some embodiments, the aptazyme functions to change configuration to capture a specific molecule, only in the presence of a second, specific, analyte.

In some embodiments, the probe comprises a detectable label. Detectable labels include any composition detectable by spectroscopic, photochemical, biochemical, immunochemical, electrical, optical, or chemical means. Illustrative useful labels include, but are not limited to, fluorescent nanoparticles (e.g., quantum dots (Qdots)), metal nanoparticles, including but not limited to gold nanoparticles, silver nanoparticles, platinum nanoparticles, fluorescent dyes (e.g., fluorescein, texas red, rhodamine, green fluorescent protein, and the like, see, e.g., Molecular Probes, Eugene, Oregon, USA), radiolabels (e.g., $^3$H, $^{125}$I, $^{35}$S, $^{14}$C, $^{32}$P, $^{99}$Tc, $^{203}$Pb, $^{67}$Ga, $^{68}$Ga, $^{72}$As, $^{111}$In, $^{113m}$In, $^{97}$Ru, $^{62}$Cu, 64lCu, $^{52}$Fe, $^{52m}$Mn, $^{51}$Cr, $^{186}$Re, $^{188}$Re, $^{77}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, $^{111}$Ag, and the like), enzymes (e.g., horse radish peroxidase, alkaline phosphatase and others commonly used in an ELISA), various colorimetric labels, magnetic or paramagnetic labels (e.g., magnetic and/or paramagnetic nanoparticles), spin labels, radio-opaque labels, and the like.

Alternatively or additionally, the probe can bind to another particle that comprises a detectable label. In some embodiments, the probes provide a detectable signal at the detection zone (e.g., test line, control line, test region, control region). In some embodiments, the detectable label/property comprises one or more of a colorimetric label/property, a fluorescent label/property, an enzymatic label/property, a colorigenic label/property, and/or a radioactive label/property. In some embodiments, the probe is a gold nanoparticle and the detectable property is a color. In some embodiments, the color is orange, red or purple.

Sample Collection

In various embodiments the sample to be assayed using the devices and methods described herein comprises a biological sample. Illustrative biological samples include, but are not limited to biofluids such as blood or blood fractions, lymph, cerebrospinal fluid, seminal fluid, urine, oral fluid, vaginal fluid, and the like, tissue samples, plaque samples, vaginal swab samples, endocervical swab samples, cell samples, tissue or organ biopsies or aspirates, histological specimens, and the like.

Where the biological sample comprises a tissue, in certain embodiments, the tissue may be lysed, homogenized, and/or ground and, optionally suspended in a sample solution. Where the biological sample comprise a biological fluid the fluid may be assayed directly or suspended in a sample solution prior to assay. In certain embodiments the sample solution may act to preserve or stabilize the biological sample or components thereof, and/or may act to extract or concentrate the biological sample or components thereof. In certain embodiments the sample solution may comprise a buffer, optionally containing preservatives, and/or enzymes (protease, nuclease, etc.), and/or surfactants, and/or ATPS components.

In certain embodiments, particular in point-of-care embodiments, the sample may be applied to the assay device immediately or after a modest time interval. In certain embodiments the sample may be delivered to a remote testing facility where the assay is run.

Methods and devices for collecting biological samples are well known to those of skill in the art, e.g., as illustrated below:

Oral Fluid Collection

Oral fluid can be collected by drooling into an empty vial, then transferring the fluid to the concentration component of the assay.

Oral fluid can also be collected using a swab and/or collection pad. For example, a swab or a collection pad can be placed in the user's mouth to soak up the oral fluid. The swab or the collection pad may contain compounds, such as peppermint extract, or a sour extract, to stimulate oral fluid production. The swab or collection pad can also act as a filter to remove food debris, contaminants, or mucus that may affect the downstream concentration and detection steps. In certain embodiments the oral fluid in the swab or collection pad can be extracted and mixed with aqueous two-phase components (ATPS) components for concentration. Extraction of the oral fluid from the collection device can be accomplished, for example, by applying physical pressure to the swab/pad to squeeze the fluid out, or by capillary action to introduce the fluid to the concentration component. Another configuration corresponds to the ATPS components being dehydrated downstream of the swab or collection pad so that no further user interaction is necessary.

Plaque Collection

Plaque can be collected by brushes, swabs, or picks on the surfaces of teeth, underneath gum, or between teeth. In certain embodiments the collected plaque can then be mixed in buffer or an ATPS solution for subsequent concentration.

Urine Collection

In various embodiments urine can be obtained with a collection cup. The collected urine can then be mixed in an ATPS solution for subsequent concentration, or applied directly onto the device if ATPS components are dehydrated in the concentration component. In a catheterized subject, urine can be obtained from the catheter or from the catheter receiving bag.

Vaginal/Endocervical Swab

Target analytes on the vaginal or cervical surface and/or in vaginal fluid can be collected by commercially available swabs. The collected swab can be placed in a buffer to release the target, or placed in the ATPS solution for direct concentration of the target biomolecules.

Blood Collection

Blood can be collected by pin (lancet) prick and collection in a capillary tube, by syringe, and the like.

Illustrative Analytes.

While essentially any analyte can be detected and/or quantified using the assay devices and methods described herein, in certain embodiments, the analyte is a clinically relevant analyte (e.g., a bacterium, a fungus, a protozoan, an amoeba, a virus, and the like).

Clinically relevant targets are well known to those of skill in the art.

Clinically Important Bacteria in Vaginal Fluids

Finding *Trichomonas vaginalis*, bacterial vaginosis and *Actinomyces* infections in vaginal fluid or tissue samples, pap smears might be considered an indication for treatment without performing other diagnostic tests. Treatment of asymptomatic infections can prevent complications in selected patients. *Candida* can be a commensal bacteria in the vagina, therefore asymptomatic patients may not require treatment. Detection of a higher rate of *Trichomonas vaginalis* and *candida* infection in intrauterine device (IUD) users shows that IUDs can increase the risk of vaginal infections and associated complications.

Gonorrhea is a bacterial infection caused by the organism *Neisseria gonorrheae* and is a clinically important pathogen. Similarly, *Chlamydia*, caused by *Chlamydia trachomatis* and syphilis, caused by *Treponema pallidum* are important sexually transmitted disease whose rapid diagnosis is desirable.

Clinically Important Bacteria in Urine

*Escherichia coli* and *Proteus* sp. are bacterial pathogens that when found in urine are typically indicative of urinary tract infections.

Clinically Important Bacteria in the Oral Cavity

Gram-negative oral anaerobes have frequently been associated with periodontal disease, some species more frequently than others. Such anerobes include, but are not limited to *Prevotella* species (e.g., *Pr. intermedia, Pr. nigrescens, Pr. melaninogenica, Pr. veroralis*, and the like) and *Porphyromonas* species (e.g., *Porph. gingivalis*).

Additionally *Streptococcus mutans* has been implicated in the formation of dental caries. Additional clinically important bacteria of the instant disclosure include but are not limited to *Actinomyces viscosus, Lactobacillus casei, Staphylococcus aureus, Candida albicans, Lactobacillus acidophilus, Capnocytophaga gingivalis, Fusobacteriun nicleatum*, or *Bacteroides fortsythus*.

It will be recognized that these pathogens are illustrative and non-limiting. One of skill will recognize that the assay devices and methods described herein can be used to detect and/or to quantify numerous other analytes.

Kits.

In certain embodiments kits are provided for use of the devices and/or practice of the methods described herein. In certain embodiments a kit for the detection and/or quantification of an analyte is provided where the kit comprises a container containing an assay device as described herein. In certain embodiments the kit additionally contains a collection device for collecting a sample. In certain embodiments the collection device comprises a device for collecting oral fluid, a device for collecting blood, a urine collection device, a device for collecting vaginal fluid or from a vaginal swab or from an endocervical swab, or a device for collecting an environmental sample.

In certain embodiments the kits additionally contain reagents such as buffers, solvents, components of an ATPS system, detection reagents, and the like.

In certain embodiments the kits additionally contain instructional materials providing methods (e.g., protocols) for use of the assay devices provided therein. Often and typically the instructional materials are provided in written form and can be printed on the kit components themselves (e.g. on the cover of a box, container, or on an envelope, or can be provided as an insert/instructional page or booklet. While the instructional materials typically comprise written or printed materials they are not limited to such. Any medium capable of storing such instructions and communicating them to an end user is contemplated. Such media include, but are not limited to electronic storage media (e.g., magnetic discs, tapes, cartridges, chips, flash memory), optical media (e.g., CD ROM), and the like. Such media may include addresses to internet sites that provide such instructional materials.

EXAMPLES

The following examples are offered to illustrate, but not to limit the claimed invention.

Example 1

Detection of *Streptococcus mutans*

Goal

We incorporated ATPS and LFA into a single paper-based diagnostic device used to detect *Streptococcus mutans* (*S. mutans*), which is the dominant bacterium that could lead to dental caries (cavities). Previously, we were able to use a micellar ATPS to achieve 10-fold concentration of *S. mutans* and improve the detection limit of LFA by 10-fold. In these studies, we examined other systems for this process. Specifically, we investigated the PPG/salt ATPS, which phase separates more quickly than the micellar ATPS and the polyethylene glycol (PEG)/salt ATPS in test tube solutions. The PPG/salt ATPS also requires less salt to achieve phase separation which provides an even more suitable environment for biomolecules to bind to the probes and for the probes to bind at the test line.

Methods and Materials

Preparing the Anti-*S. mutans* DGNPs

The pH of a 1 mL dextran-coated gold nanoparticle (DGNP) solution was first adjusted to pH 9 using 1.5 N NaOH. Subsequently, 16 µg of mouse monoclonal *S. mutans* antibody were added to the gold solution and mixed for 30 min on a shaker. To prevent nonspecific binding of other proteins to the surfaces of the colloidal gold nanoparticles, 200 µL of a 10% w/v bovine serum albumin (BSA) solution were added to the mixture and mixed for 20 min on a shaker. To remove free, unbound antibodies, the mixture was then centrifuged for 30 min at 4° C. and 9,000 rpm, followed by resuspending the pellet of DGNPs in 200 µL of a 1% w/v BSA solution. The centrifugation and resuspension steps were repeated two more times, and after the third centrifugation, the pellet of DGNPs was resuspended in 100 µL of 0.1 M sodium borate buffer at pH 9.0.

Detection Using LFA

LFA test strips utilizing the sandwich assay format were assembled in a similar manner to our previous studies described in copending PCT Application No: PCT/US2015/019297, filed on Mar. 6, 2015, which is incorporated herein by reference for the assay formats and reagents described herein. In this format, immobilized *S. mutans* antibody constituted the test line and immobilized secondary antibodies specific to the primary antibody constituted the control line.

To verify the detection limit of *S. mutans* with LFA, DGNPs were added to a sample solution and allowed to bind *S. mutans* present in the sample. A sample suspension containing some saliva, DGNPs, and known concentrations of *S. mutans* were mixed in a test tube. The LFA test strip was inserted vertically into each sample suspension, which wicked upward through the strip via capillary action towards the absorbent pad. Images of the test strips were taken after 10 min in a controlled lighting environment.

Detection Using LFA with ATPS

Figure 5:
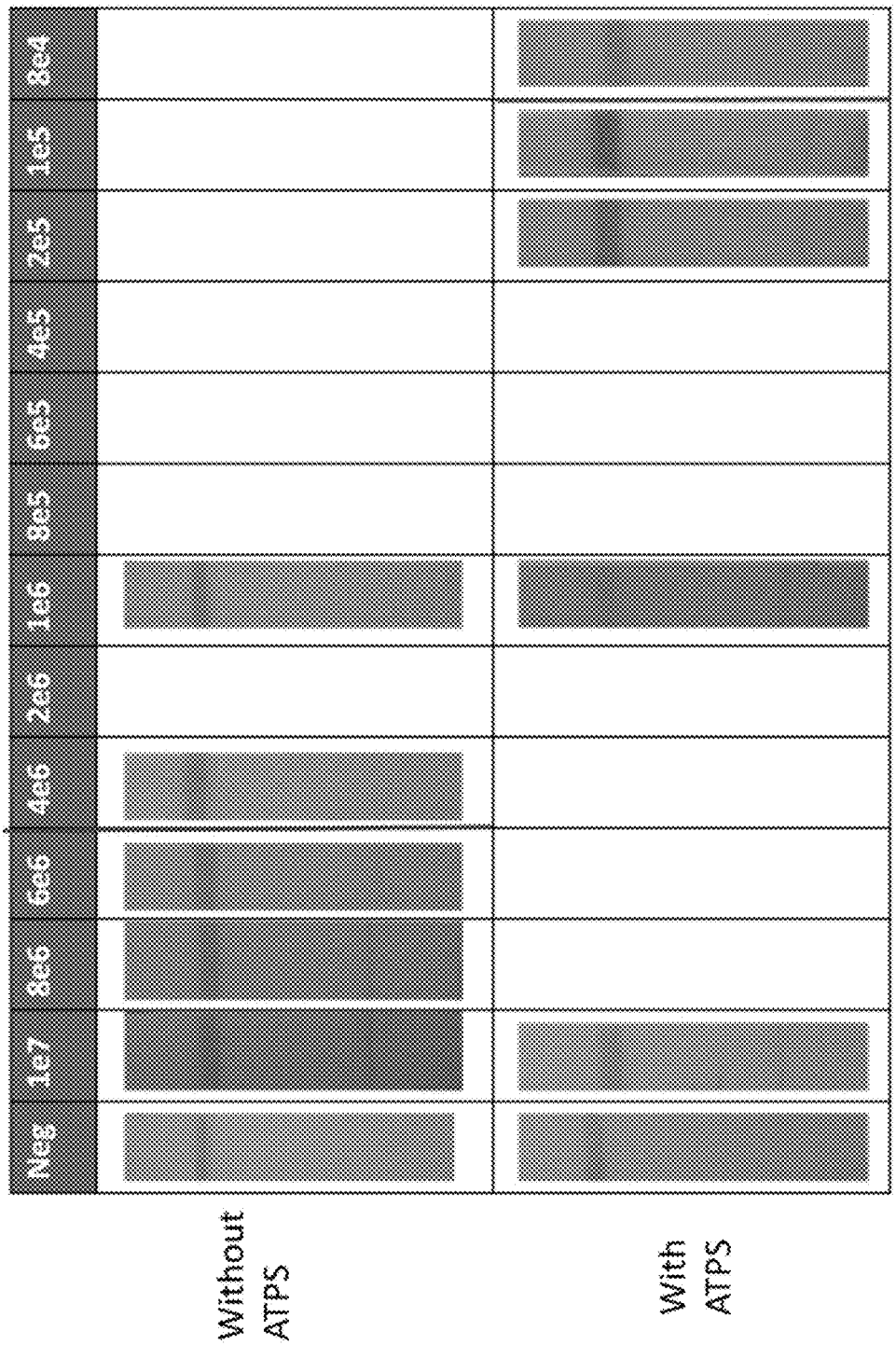
FIG. 5 illustrates the concentration and detection of S. mutans using PPG/salt ATPS and LFA.

A PPG/potassium phosphate ATPS sample solution with a top phase to bottom phase volume ratio of 60:1 was prepared, which consisted of known concentrations of *S. mutans*. The ATPS sample solutions were incubated at room temperature for 10 min to allow phase separation to occur. The bottom PEG-poor phase which contained concentrated *S. mutans* was extracted and incubated with anti-*S. mutans* DGNP. The LFA test strip was inserted vertically into the resulting mixture, and images of the test strips were taken after 10 min in a controlled lighting environment (FIG. 5).

We successfully concentrated *S. mutans* using the new ATPS and drastically improved the concentration factor from 10-fold to 60-fold. The phase separation time also improved from hours (in a test tube solution containing a micellar ATPS) to only 10 min (in a test tube solution containing the PPG/salt ATPS). We then demonstrated this enhancement can be applied to the subsequent detection step and showed a 60-fold improvement in detection limit of LFA (FIG. 5), reaching $1\times10^5$ cells/mL. The entire assay was completed within 20 min.

Example 2

Detection of *Streptococcus mutans* in Plaque

Goal

We investigated the feasibility of detecting *S. mutans* in plaque.

Methods and Materials

Toothpicks were used to extract plaque from subjects. The collected plaque was then dissolved in phosphate-buffered saline (PBS). LFA test strip, prepared as described above, was applied to the resulting solution. Images of the test strips were taken after 10 min in a controlled lighting environment.

Results.

Figure 6:
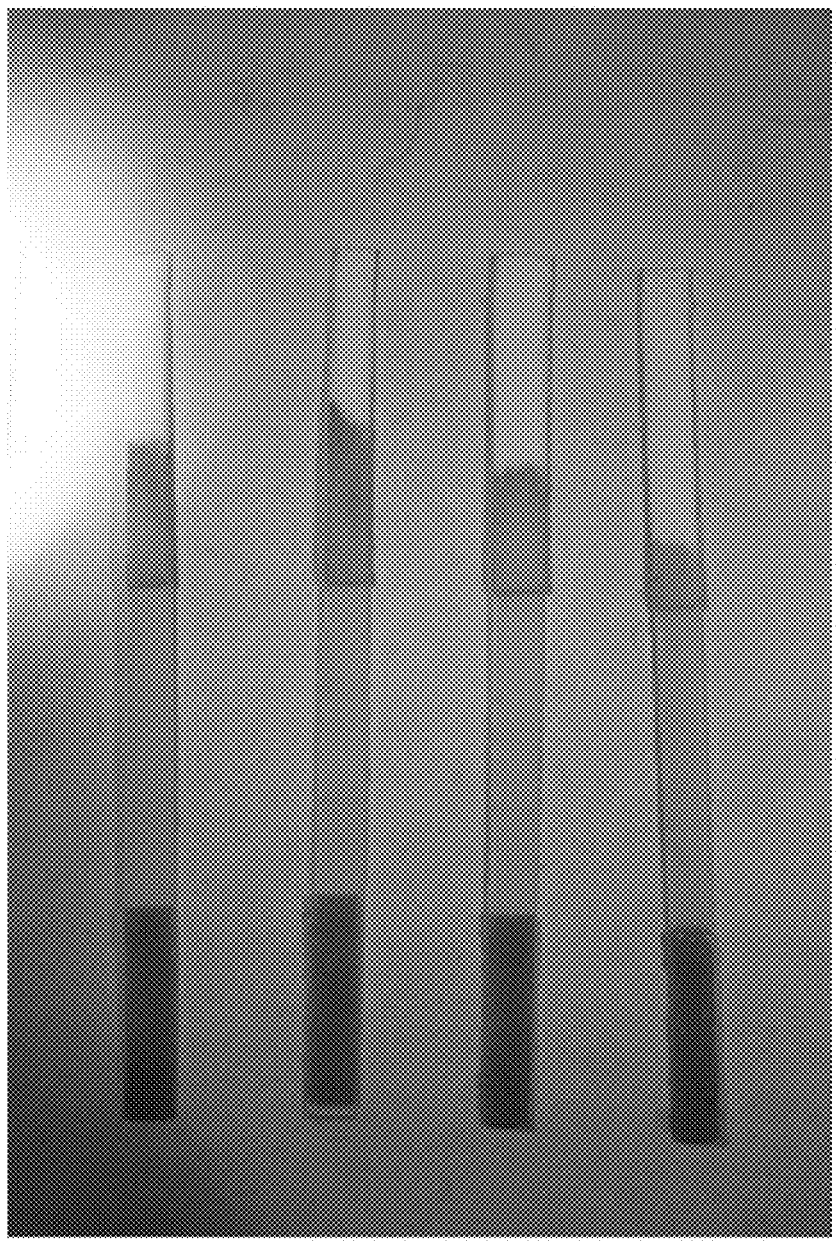
FIG. 6 illustrates the detection of S. mutans in plaque from 4 subjects. The higher test line intensity indicates a greater concentration of S. mutans in the subject.

FIG. 6 shows the detection of *S. mutans* in plaque from 4 subjects. The higher test line intensity indicates a greater concentration of *S. mutans* in the subject.

Figure 7:
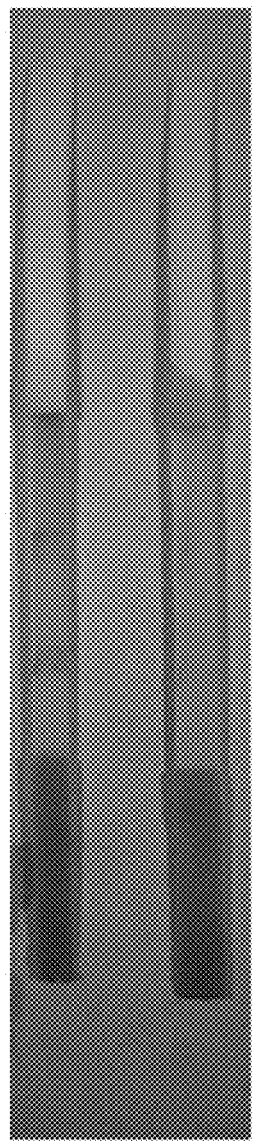
FIG. 7 illustrates the detection of S. mutans in plaque before and after brushing teeth. The result indicated that brushing teeth is effective in removing S. mutans and lowering the risk to develop dental caries.

FIG. 7 shows the detection of *S. mutans* in plaque before and after brushing teeth. The results indicated that brushing teeth is effective in removing *S. mutans* and lowering the risk to develop dental caries.

Example 3

*Chlamydia* Detection

Goal

We incorporated ATPS and LFA into a single paper-based diagnostic device that could be used to detect *Chlamydia trachomatis* (*C. trachomatis*) in a patient urine or a patient swab sample.

Methods and Materials

Preparing the Anti-*C. trachomatis* DGNPs

The pH of a 1 mL dextran-coated gold nanoparticle (DGNP) solution was first adjusted to pH 9 using 1.5 N NaOH. Subsequently, 16 µg of mouse monoclonal *C. trachomatis* antibody were added to the colloidal gold suspension and mixed for 30 min on a shaker. To prevent nonspecific binding of other proteins to the surfaces of the colloidal gold nanoparticles, 200 µL of a 10% w/v bovine serum albumin (BSA) solution were added to the mixture and mixed for 20 min on a shaker. To remove free, unbound antibodies, the mixture was then centrifuged for 30 min at 4° C. and 9,000 rpm, followed by resuspending the pellet of DGNPs in 200 µL of a 1% w/v BSA solution. The centrifugation and resuspension steps were repeated two more times, and after the third centrifugation, the pellet of DGNPs was resuspended in 100 µL of 0.1 M sodium borate buffer at pH 9.0.

Detection Using LFA

LFA test strips utilizing the sandwich assay format were assembled in a similar manner to our previous studies. In this format, immobilized *C. trachomatis* antibody constituted the test line and immobilized secondary antibodies specific to the primary *C. trachomatis* antibody constituted the control line.

To verify the detection limit of *C. trachomatis* with LFA, DGNPs were added to a sample solution and allowed to bind *C. trachomatis* present in the sample. A suspension containing DGNPs in phosphate-buffered saline (PBS) and a solution containing a known concentration of *C. trachomatis* in PBS were mixed in a test tube. The LFA test strip was inserted vertically into the sample solution, which wicked through the strip via capillary action upward towards the absorbance pad. Images of the test strips were taken after 10 min in a controlled lighting environment.

Detection Using LFA with ATPS

A PEG/potassium phosphate ATPS sample solution with a top phase to bottom phase volume ratio of 9:1 was prepared, which consisted of known concentrations of *C. trachomatis*. The ATPS sample solutions were incubated at room temperature for 30 min to allow phase separation to occur. The bottom PEG-poor phase which contained concentrated *C. trachomatis* was extracted and incubated with anti-*C. trachomatis* DGNP. The LFA test strip was inserted vertically into the resulting mixture. Images of the test strips were taken after 10 min in a controlled lighting environment.

Results

Figure 8:
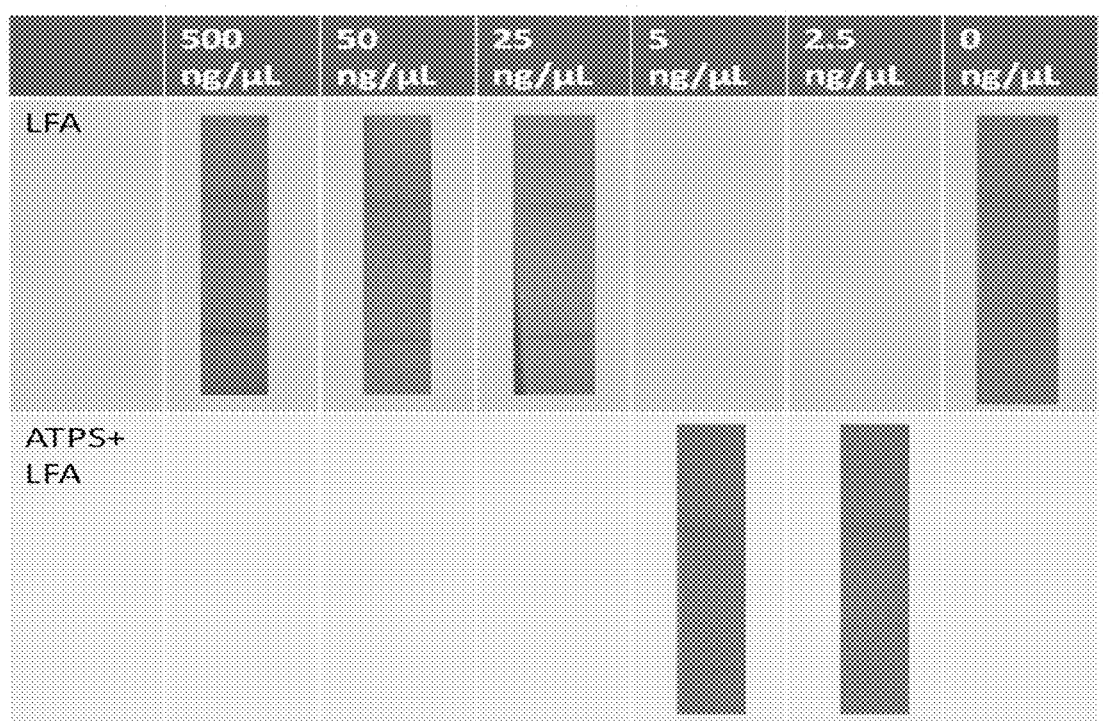
FIG. 8 illustrates the detection of C. trachomatis in PBS using LFA alone and using ATPS with LFA.
Figure 9:
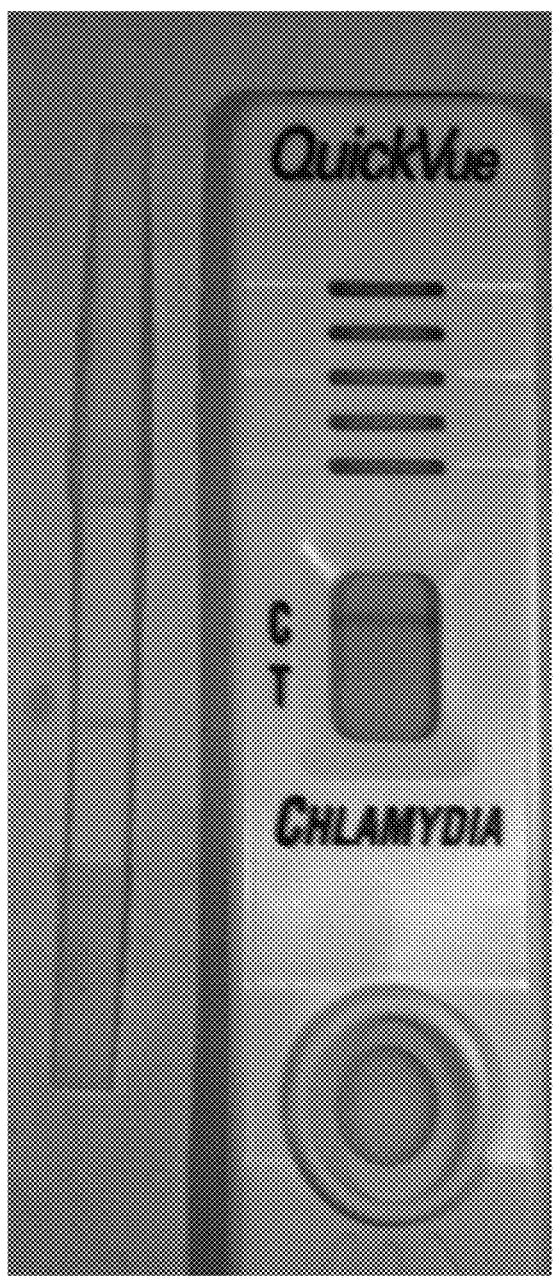
FIG. 9 illustrates the performance of a device described herein compared to an FDA approved, commercially available Chlamydia LFA in a clinical urine sample collected from a C. trachomatis positive patient. Our device is able to provide a true positive result (the presence of the test line), while the commercial test gave a false negative result (the absence of the test line).

FIG. 8 shows detection of *C. trachomatis* in PBS using LFA alone and using ATPS with LFA. FIG. 9 shows the performance of our device compared with an FDA approved, commercially available *chlamydia* LFA for a clinical urine sample collected from a *C. trachomatis* positive patient. Our device is able to provide a true positive result (the presence of the test line), while the commercial test gave a false negative result (the absence of the test line).

Example 4

An Illustrative Diagnostic Device with Dehydrated ATPS Components

Figure 11:
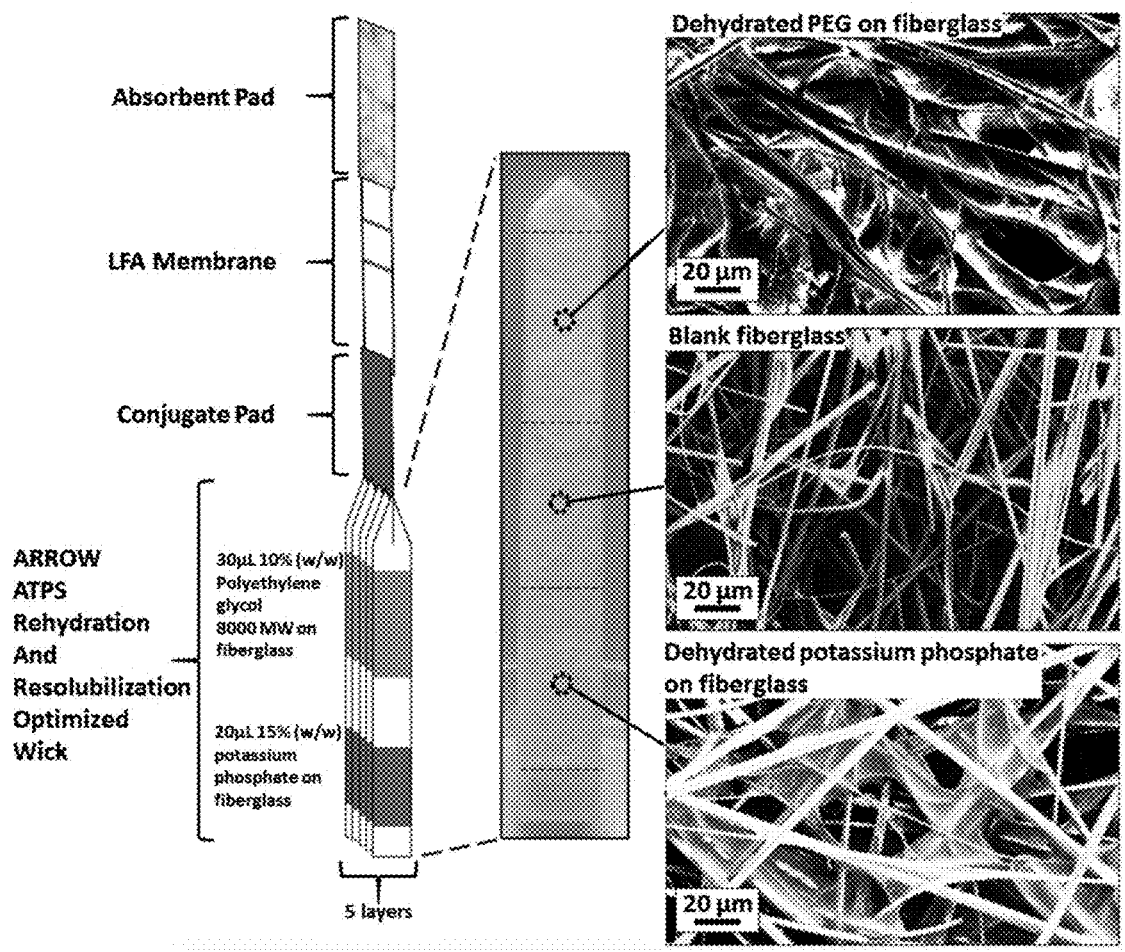
FIG. 11. The integrated ARROW and LFA diagnostic design. (Left) Design layout of the integrated ARROW and LFA. (Middle) Image of the ARROW. (Right) SEM images of the dehydrated PEG on fiberglass, blank fiberglass, and dehydrated potassium phosphate on fiberglass. The top and bottom tips of the fiberglass paper sheet are also blank fiberglass.

In one illustrative embodiment, a dehydrated ATPS diagnostic device (FIG. 11) is comprised of two major components: The ATPS rehydration and resolubilization optimized wick (ARROW) and the standard LFA. In the illustrated embodiment, the ARROW consists of 5 fiberglass paper sheets layered together. Considering that the function of the ATPS is to concentrate the target pathogen, it was important that the ARROW was able to wick up a large volume of sample solution. Each sheet is first pre-treated with BSA in order to prevent non-specific binding of *C. trachomatis* during sample solution flow. After pre-treatment, 20 µL of 15% (w/w) potassium phosphate was dehydrated in the upstream portion of each fiberglass sheet, while 30 µL of 10% (w/w) PEG 8000 was dehydrated in the downstream portion of each fiberglass sheet. It is important to leave blank space between the dehydrated PEG and the tip of the sheet to allow for PEG-poor phase collection, which contains the concentrated pathogen. The downstream tip of each sheet is tapered to form a point, which facilitates proper transition of the liquid into the conjugate pad.

The LFA portion of the diagnostic consisted of the conjugate pad containing the colorimetric indicator, connected to a nitrocellulose membrane with printed primary and secondary antibodies, and followed by an absorbance pad. The LFA portion interfaced with the ARROW by fitting a small upstream portion of the conjugate pad perpendicularly into a slit that had been cut in the ARROW.

SEM images (FIG. 11) of the blank fiberglass region of the fiberglass paper shows a porous fiber-based matrix structure. The dehydrated PEG and potassium phosphate regions show a similar porous structure, with the addition of web-like connections, which it is believed contains a majority of their respective ATPS components. These images demonstrate that the process of dehydration does not significantly deform the porous structure of the fiberglass paper, which is critical for proper wicking of the sample fluid.

Importance of the Rehydration Order of PEG and Potassium Phosphate

The effect of the PEG and potassium phosphate rehydration order on the phase separation behavior within the paper was investigated. To do this, a suspension comprised of BSA-DGNPs and Brilliant Blue dye was utilized which allowed visualization of the phase separation process as the suspension flowed through the paper. In short, the BSA-DGNPs partition into the PEG-poor phase indicated by the burgundy/light purple color, while the blue dye partitions into the PEG-rich phase indicated by the light blue color. Regions of macroscopically mixed domains contained both BSA-DGNPs and blue dye, indicated by the dark blue/dark purple color. During fiberglass paper preparation, the location of the dehydrated ATPS components was altered, such that one condition had the dehydrated potassium phosphate located upstream of the dehydrated PEG (denoted "Salt→PEG"), while the other condition had the dehydrated PEG located upstream of the dehydrated potassium phosphate (denoted "PEG→Salt").

Figure 12:
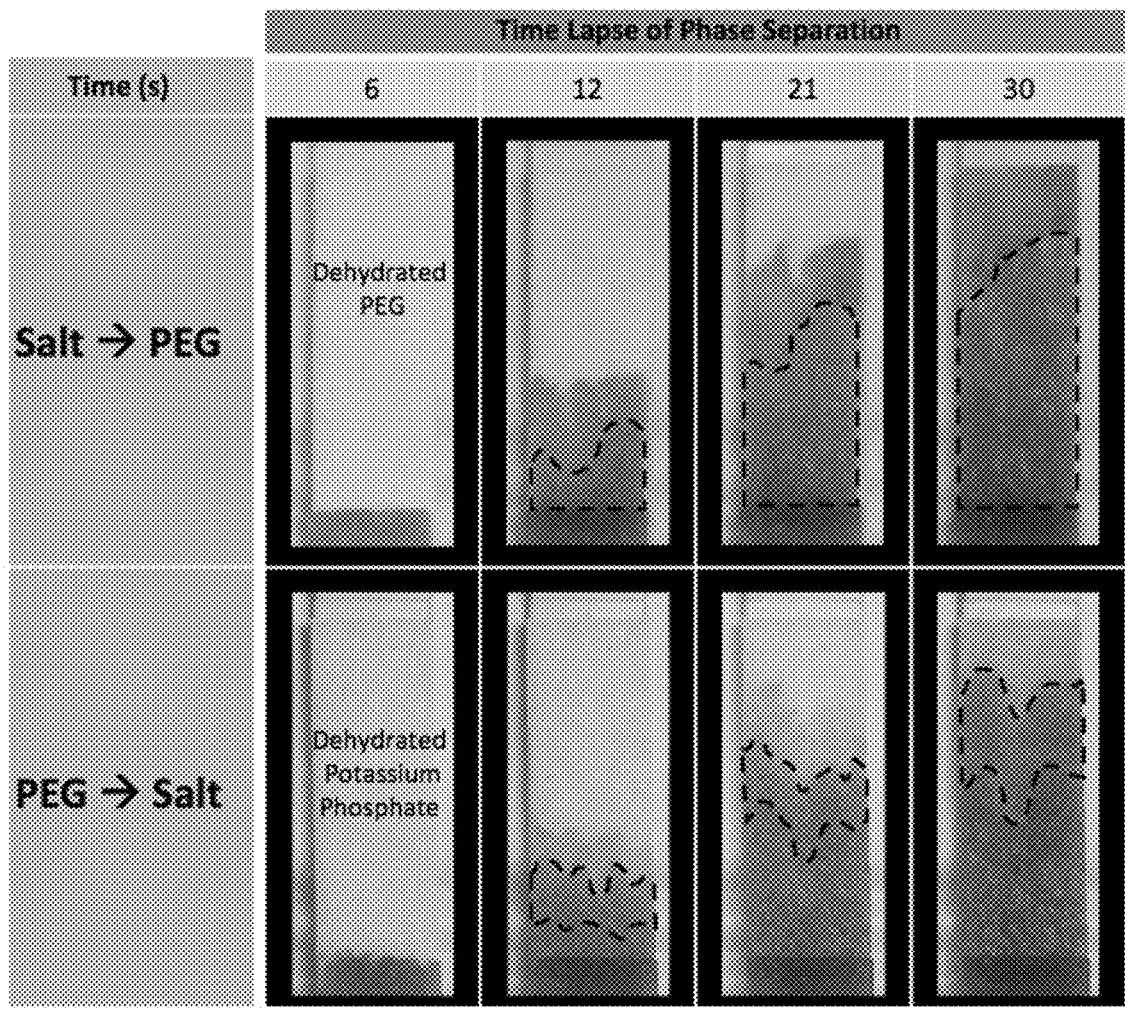
FIG. 12. Demonstrating the importance of ATPS component rehydration order. Time-lapse visualization of phase separation within a single sheet of the ARROW design when the rehydration order of the PEG and potassium phosphate are switched. Close up images are shown of the downstream region where phase separation occurred, and therefore, the first image is at t=6 instead of t=0. The dotted line (- - -) encompasses the region of the paper that predominantly contained the PEG-rich phase, identified by the light blue color. Visualization and identification of the PEG-rich phase, PEG-poor phase, and macroscopically mixed domain regions were accomplished by flowing a suspension of BSA-DGNPs and Brilliant Blue dye.

From these results (FIG. 12), we note two interesting observations. First, the leading PEG-poor fluid had a significantly darker burgundy color in the 'Salt→PEG' condition compared to the 'PEG→Salt' condition, indicating that the 'Salt→PEG' condition contained more BSA-DGNPs in the leading fluid, and therefore, is more effective at concentrating large species. Second, the PEG-rich phase, the area identified by the dashed lines in FIG. 12, exhibited significantly more volumetric growth over time in the 'Salt→PEG' condition compared to the PEG-rich phase in the 'PEG→Salt' condition. This suggests that in the 'Salt→PEG' condition, the newly formed PEG-poor domains are able to get out of the mixed domain region and more efficiently pass through the trailing PEG-rich phase and collect into the leading PEG-poor phase. is results in the PEG-rich phase becoming larger as the mixed domains region becomes smaller. One possible reason for this phenomenon is the formation of PEG-poor channels within the PEG-rich phase that connect to the leading PEG-poor phase. Research in multiphase fluid flow within porous media has found that less viscous fluids will develop preferred channels when displacing more viscous fluids.

Figure 13:
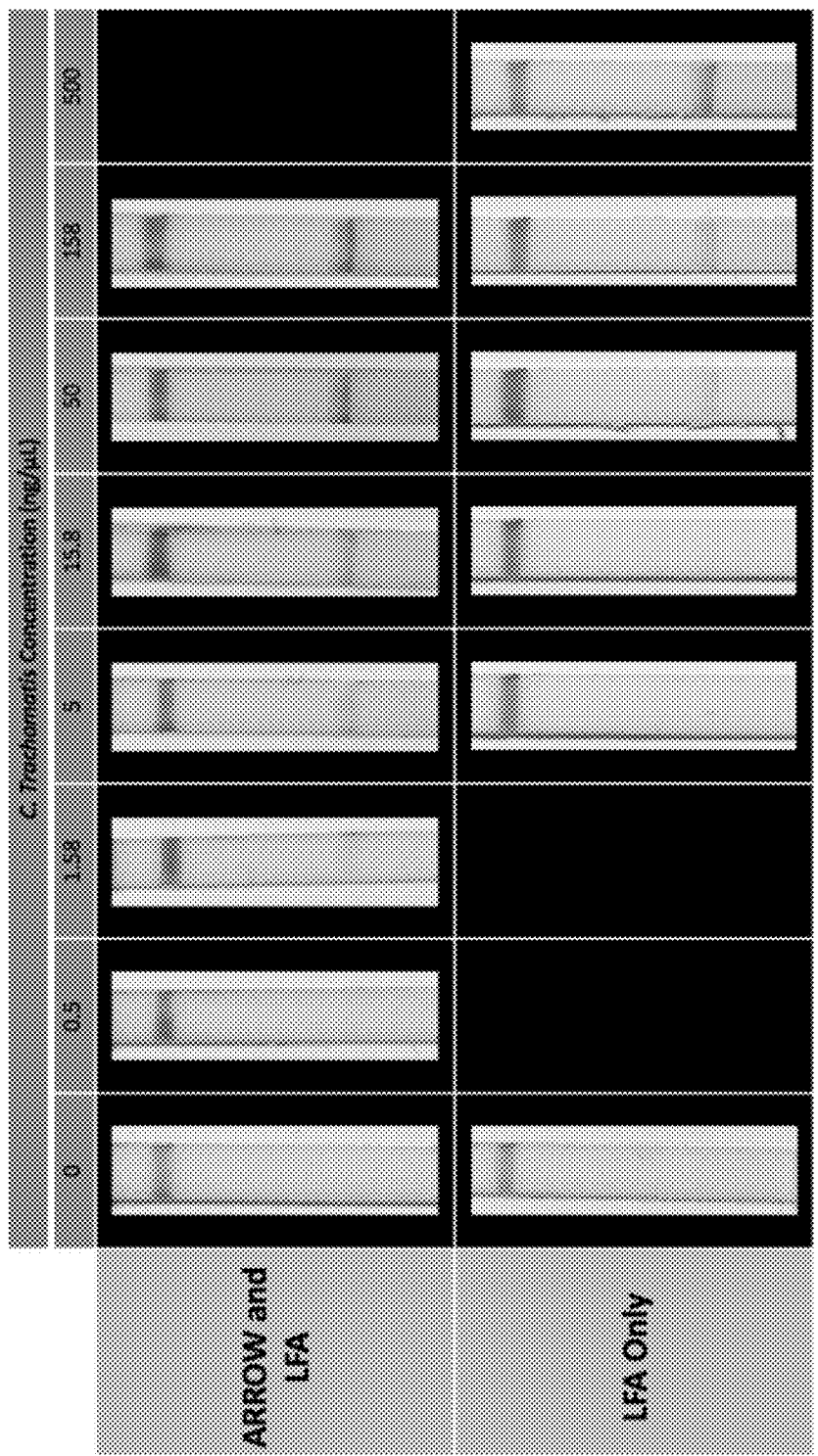
FIG. 13. Improvement in the limit of detection of C. trachomatis LFA by incorporation of the ARROW. Comparison of LFA results at varying C. trachomatis concentrations, with and without the ARROW. Test lines are located on the bottom of the LFA strips while the control lines are located on the top of the LFA test strips. Negative control results are shown in the left most panels for 0 ng/µL C. trachomatis.

Improved Limit of Detection for *C. trachomatis* Using the Integrated LFA and ARROW We demonstrated that our ARROW design effectively concentrated a *C. trachomatis* sample suspension, resulting in an improved limit of detection for LFA. To do this, we ran sample solutions of varying initial concentrations of *C. trachomatis* on LFA test strips, with and without the ARROW component. We see from the results of the LFA panel (FIG. 13) that the LFA only system started showing false negative results at around 15.8 ng/µL *C. trachomatis* while the integrated LFA and ARROW system started showing false negative results at around 1.58 ng/µL *C. trachomatis*. This visually demonstrates a 10-fold improvement in the limit of detection.

Figure 14:
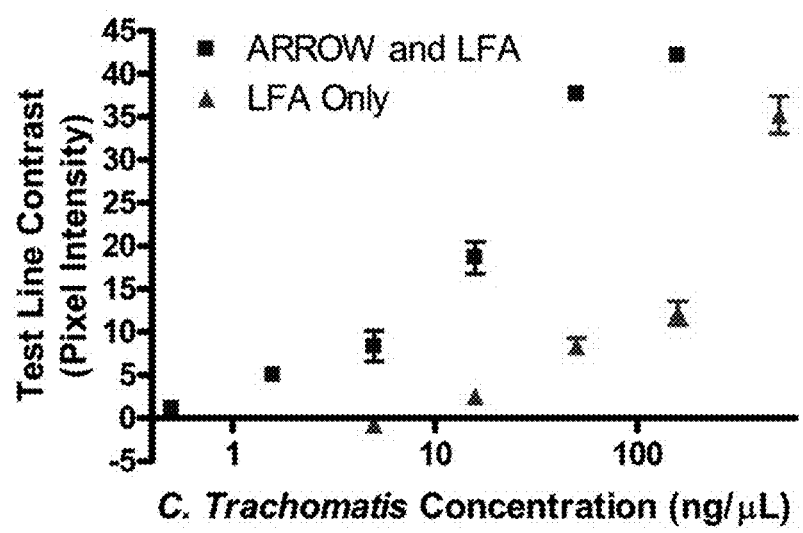
FIG. 14. Quantification of test line intensities. Plot of the quantified LFA test line intensities for the ARROW and LFA system and the LFA only system.

We also quantified the pixel contrast of the test lines on the LFA images using a customized MATLAB program (FIG. 14). This allowed us to quantitatively assess the improvement in the limit of detection. For any given concentration of *C. trachomatis*, we see a significant increase in the test line intensity for the integrated ARROW and LFA system compared to the LFA only system. For example, at 50 ng/µL *C. trachomatis*, the LFA only condition had a pixel contrast intensity of 8.3±1.7, while the integrated ARROW and LFA had a pixel contrast intensity of 37.6±0.6. Furthermore, we also see confirmation of our panel results where the same test line intensity 8.3 was observed at the limits of detection noted in the panels (50 ng/µL for LFA alone and 5 ng/µL for integrated ARROW and LFA).

Figure 15:
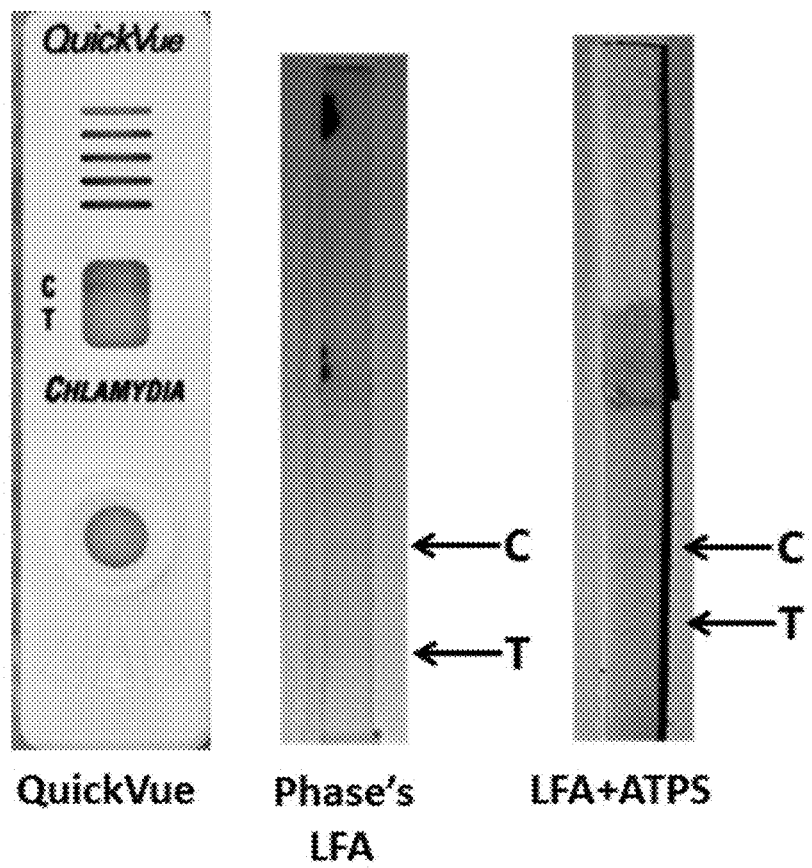
FIG. 15. Representative result (sample #4, Table 2) of the head-to-head comparison between QuickVue, Phase's LFA, and Phase's LFA+ATPS. The presence of the test line (T) indicates a true positive result. Only our LFA+ATPS had a visible test line indicating a true positive result.

We wanted to verify that these quantities were in fact physiologically relevant. Using remnant clinical urine specimens, our urine-based LFA (by itself) had poor sensitivity, consistent with what we obtained with the QuickVue test for samples in urine. However, when the urine-based LFA was integrated with ATPS, we demonstrated a significant improvement in sensitivity, recognizing 87.5% (14/16) CT+ urine samples with a positive result. (Table 2). An example of this head-to-head comparison is shown in FIG. 15.

TABLE 2

A summary of a performance comparison study between FDA approved QuickVue, phase diagnostics' LFA-only test, and phase diagnostics' LFA + ATPS test in the detection of ct in remnant clinical urine samples. All samples were ct+ confirmed by a nucleic acid amplification test (NAAT). In contrast to the frozen samples, neat samples were freshly collected ones.

| Sample | Type | NAAT | QuickVue | Phase's LFA | Phase's LFA + ATPS |
|---|---|---|---|---|---|
| 1 | Neat | + | − | + | + |
| 2 | Neat | + | − | − | + |
| 3 | Neat | + | − | − | + |
| 4 | Neat | + | − | − | + |
| 5 | Neat | + | − | − | + |
| 6 | Neat | + | − | − | + |
| 7 | Frozen | + | − | − | + |
| 8 | Frozen | + | − | − | + |
| 9 | Frozen | + | − | − | + |
| 10 | Frozen | + | − | − | + |
| 11 | Frozen | + | − | − | − |
| 12 | Frozen | + | − | − | − |
| 13 | Frozen | + | − | − | + |
| 14 | Frozen | + | − | − | + |
| 15 | Frozen | + | − | − | + |
| 16 | Frozen | + | − | − | + |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of concentrating an analyte using an aqueous two-phase system, said method comprising:
   providing a porous matrix comprising salt-polymer aqueous two-phase system (ATPS) comprising a mixed phase solution that separates into a first phase solution and a second phase solution as said ATPS moves through said porous matrix wherein said ATPS is provided as a dehydrated salt and a dehydrated polymer that when rehydrated form said mixed phase of an aqueous two-phase system, where said dehydrated salt is disposed in said porous matrix upstream from said dehydrated polymer;
   applying a sample solution comprising said analyte to said porous matrix where said sample solution rehydrates the dehydrated salt and dehydrated polymer to form the mixed phase solution that separates into a first phase solution and a second phase solution as said ATPS moves through said porous matrix and concentrates the analyte into the first phase solution or the second phase solution or an interface between the first phase solution and second phase solution.

2. The method of claim 1, wherein said porous matrix comprises a material selected from the group consisting of fiberglass, cellulose, and nitrocellulose.

3. The method of claim 2, wherein said porous matrix comprises fiberglass.

4. The method of claim 1, wherein said polymer comprises a polymer selected from the group consisting of polyethylene glycol (PEG), polypropylene glycol, and dextran.

5. The method of claim 4, wherein said polymer comprises polyethylene glycol.

6. The method of claim 1, wherein said salt comprises a salt selected from the group consisting of potassium phosphate, sodium sulfate, magnesium sulfate, ammonium sulfate, and sodium citrate.

7. The method of claim 6, wherein said salt comprises potassium phosphate.

8. The method of claim 1, wherein:
   said polymer comprise polyethylene glycol (PEG); and
   said salt comprises potassium phosphate.

9. The method of claim 8, wherein said porous matrix comprises a material selected from the group consisting of fiberglass, cellulose, and nitrocellulose.

10. The method of claim 9, wherein said porous matrix comprises fiberglass.

11. The method of claim 1, wherein said analyte comprises an analyte selected from the group consisting of a bacterium, a fungus, and a virus.

12. The method of claim 11, wherein said analyte comprises a bacterium.

13. The method of claim 12, wherein said analyte comprises an oral bacterium, a bacterium found in urine, a bacterium found in vaginal fluid, or a bacterium found on a vaginal swab, or a bacterium found on an endocervical swab.

14. The method of claim 13, wherein said analyte comprises an oral bacterium.

15. The method of claim 14, wherein said analyte comprises an oral bacterium selected from the group consisting of *Prevotella* sp., *Porphyromonas* sp., *Streptococcus* sp., *Actinomyces viscosus*, *Lactobacillus casei*, *Staphylococcus aureus*, *Candida albicans*, *Lactobacillus acidophilus*, *Capnocytophaga gingivalis*, *Fusobacterium nucleatum*, and *Bacteroides fortsythus*.

16. The method of claim 13, wherein said analyte comprises a bacterium found in vaginal fluid.

17. The method of claim 16, wherein said analyte comprises a bacterium selected from the group consisting of *Trichomonas* sp., *Actinomyces* sp., *Gardnerella* sp., *Neisseria* sp., *Chlamydia* sp., or *Treponema* sp.

18. The method of claim 13, wherein said analyte comprises a bacterium found in urine.

19. The method of claim 18, wherein said analyte comprises a bacterium selected from the group consisting of *E. coli*, *Proteus* sp., *Trichomonas* sp., *Actinomyces* sp., *Gardnerella* sp., *Neisseria* sp., *Chlamydia* sp., or *Treponema* sp.

* * * * *